US010588902B2

(12) United States Patent
Smith et al.

(10) Patent No.: US 10,588,902 B2
(45) Date of Patent: Mar. 17, 2020

(54) CAMPTOTHECIN DERIVATIVES AS ANTI-HIV AGENTS AND METHODS OF IDENTIFYING AGENTS THAT DISRUPT VIF SELF-ASSOCIATION

(71) Applicants: OyaGen, Inc., Rochester, NY (US); Harold C. Smith, Rochester, NY (US); Ryan P. Bennett, Clifton Springs, NY (US)

(72) Inventors: Harold C. Smith, Rochester, NY (US); Ryan P. Bennett, Clifton Springs, NY (US)

(73) Assignee: OyaGen, Inc., Rochester, NY (US)

(*) Notice: Subject to any disclaimer, the term of this patent is extended or adjusted under 35 U.S.C. 154(b) by 348 days.

(21) Appl. No.: 14/900,666

(22) PCT Filed: Jun. 24, 2014

(86) PCT No.: PCT/US2014/043974
§ 371 (c)(1),
(2) Date: Dec. 22, 2015

(87) PCT Pub. No.: WO2014/210082
PCT Pub. Date: Dec. 31, 2014

(65) Prior Publication Data
US 2016/0143900 A1 May 26, 2016

Related U.S. Application Data

(60) Provisional application No. 61/838,574, filed on Jun. 24, 2013.

(51) Int. Cl.
*A61K 31/4745* (2006.01)
*G01N 33/68* (2006.01)
*A61K 45/06* (2006.01)

(52) U.S. Cl.
CPC .......... *A61K 31/4745* (2013.01); *A61K 45/06* (2013.01); *G01N 33/6845* (2013.01);
(Continued)

(58) Field of Classification Search
None
See application file for complete search history.

(56) References Cited

U.S. PATENT DOCUMENTS

2002/0193391 A1  12/2002  Bouscarel et al.
2003/0165846 A1  9/2003  Marino et al.
(Continued)

FOREIGN PATENT DOCUMENTS

WO  1991/016904 A1  11/1991
WO  2014/055944 A1  4/2014
(Continued)

OTHER PUBLICATIONS

Li Camptothecin Inhibits Tat-Mediated Transactivation of Type 1 Human Immunodeficiency Virus, Journal of Biological Chemistry, 1994, 269 (10), pp. 7051-7054.*
(Continued)

*Primary Examiner* — Savitha M Rao
*Assistant Examiner* — Andrew P Lee
(74) *Attorney, Agent, or Firm* — FisherBroyles, LLP; Andrew K. Gonsalves, Esq.; Richard Echler

(57) ABSTRACT

The present invention relates to the use of camptothecin derivatives as anti-HIV agents that disrupt self-association of the viral infectivity factor (Vif) found in HIV and other retroviruses. The present invention also relates to methods of identifying agents that disrupt VIf self-association and methods of using these agents, including methods of treating or preventing HIV infection.

2 Claims, 29 Drawing Sheets

(52) U.S. Cl.
CPC ... *G01N 2333/15* (2013.01); *G01N 2333/163* (2013.01); *G01N 2500/02* (2013.01); *G01N 2500/10* (2013.01)

(56) References Cited

U.S. PATENT DOCUMENTS

| | | |
|---|---|---|
| 2007/0212756 A1 | 9/2007 | Greene et al. |
| 2008/0167199 A1 | 7/2008 | Zhang et al. |
| 2010/0029570 A1 | 2/2010 | Zhang et al. |
| 2015/0272959 A1 | 10/2015 | Smith et al. |
| 2015/0366984 A1 | 12/2015 | Sun |

FOREIGN PATENT DOCUMENTS

| | | |
|---|---|---|
| WO | 2014/186423 A1 | 11/2014 |
| WO | 2014/210082 A2 | 12/2014 |

OTHER PUBLICATIONS

Patani, Bioisosterism: A Rational Approach in Drug Design, Chem. Rev., 1996, 96, pp. 3147-3176.*

Zhang, T-cell differentiation factor CBF-β regulates HIV-1 Vif-mediated evasion of host restriction, Nature, Jan. 2012, 481, pp. 376-380.*

Nobeli (Hydrogen Bonding Properties of Oxygen and Nitrogen Acceptors in Aromatic Heterocycles, Journal of Computational Chemistry, 1997, 18(16), pp. 2060-2074 (Year: 1997).*

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113. (Year: 1989).*

Zuo (Small-Molecule Inhibition of Human Immunodeficiency Virus Type 1 Replication by Targeting the Interaction between Vif and ElonginC, Journal of Virology, 2012, 86(10), pp. 5497-5507. (Year: 2012).*

Cutrell, HIV prevention trial design in an era of effective pre-exposure prophylaxis, HIV Clinical Trials, 2017, 18(5-6), pp. 177-188. (Year: 2017).*

Zhang et al., "Topotecan Inhibits Human Immunodeficiency Virus Type 1 Infection through a Topoisomerase-independent Mechanism in a Cell Line with Altered Topoisomerase I," Antimicrobial Agents and Chemotherapy 41 (5):977-981 (May 1997).

Yoshikawa et al., "Novel Camptothecin Analogues that Circumvent ABCG2-Associated Drug Resistance in Human Tumor Cells," International Journal of Cancer 110:921-927 (Mar. 24, 2004).

Bala et al., "Prodrug and Nanomedicine Approaches for the Delivery of the Camptothecin Analogue SN38," Journal of Controlled Release 172:48-61 (Aug. 6, 2013).

Zhang et al., "Identification of an HIV-1 Replication Inhibitor which Rescues Host Restriction Factor APOBEC3G in Vif-APOBEC3G Complex," Antiviral Research 122:20-27 (Aug. 1, 2015).

International Search Report issued in International Counterpart Application No. PCT/US2014/043974, dated Dec. 24, 2014.

Written Opinion issued in International Counterpart Application No. PCT/US2014/043974, dated Dec. 24, 2014.

Salter et al., "Structural Insights for HIV-1 Therapeutic Strategies Targeting Vif," Trends in Biochemical Sciences 39(9):373-380 (Sep. 2014).

Hertzberg et al., "Modifications of the Hydroxy Lactone Ring of Camptothecin: Inhibitoin of Mammalian Topisomerase I and Biological Activity," J. Med. Chem. 32:715-720 (1989).

Jaxel et al., "Structure-Activity Study of the Actions of Camptothecin Derivatives on Mammalian Topoisomerase I: Evidence for a Specific Receptor Site and a Relation to Antitumor Activity," Cancer Research 49:1465-1469 (Mar. 1989).

Redinbo et al., "Crystal Structure of Human Topoisomerase I in Covalent and Noncovalent Complexes with DNA," Science 279:1504-1513 (Mar. 1998).

Xiao et al., "Effect of E-Ring Modifications in Camptothecin on Topoisomerase I Inhibition: A Quantum Mechanics Treatment," J. Org. Chem. 70:9584-9587 (Oct. 2005).

Pubmed Compound Summary for CID 60838, Irinotecan, U.S. National Library of Medicine, p. 1 (https://pubchem.ncbi.nlm.nih.gov/compound/irinotecan) (Jun. 24, 2005).

\* cited by examiner

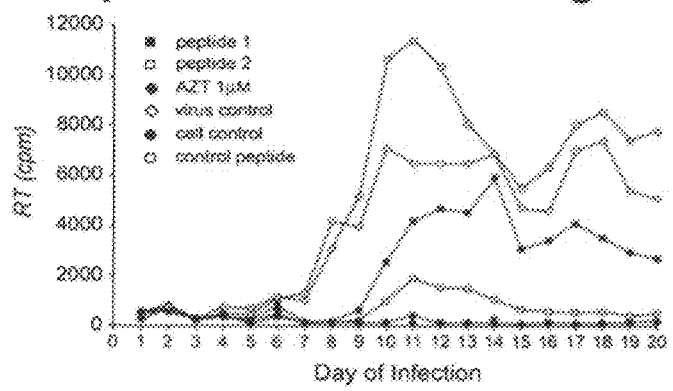
FIG. 3
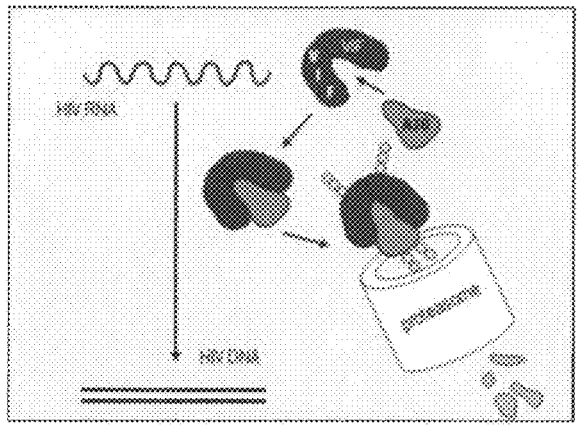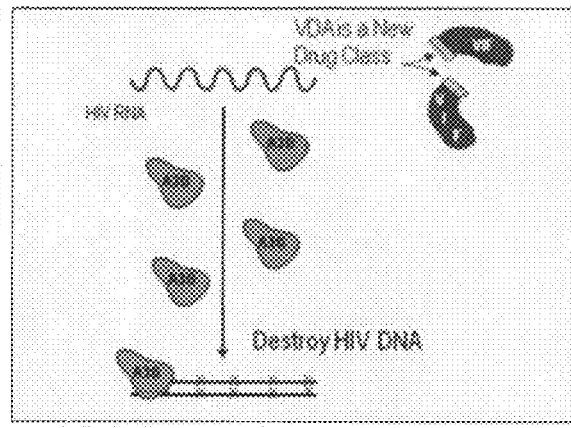
FIG. 4

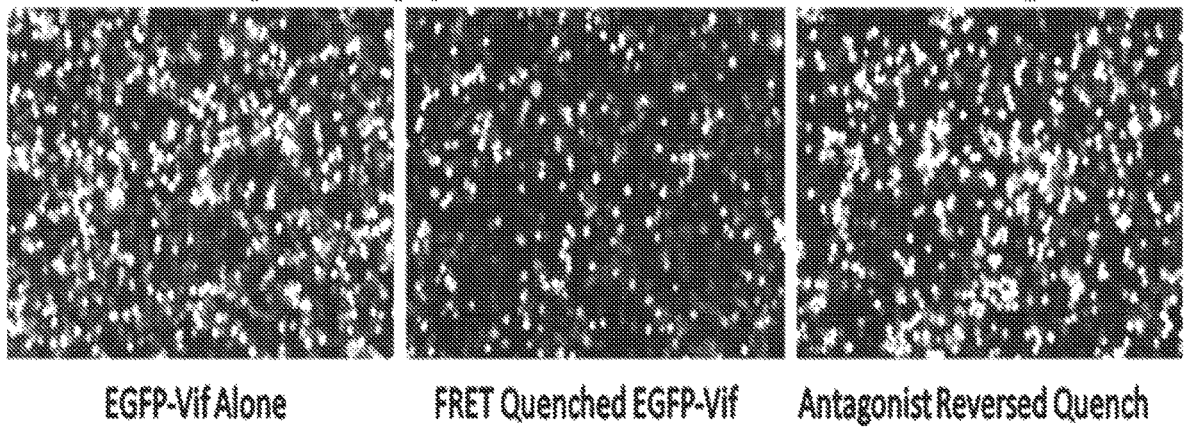
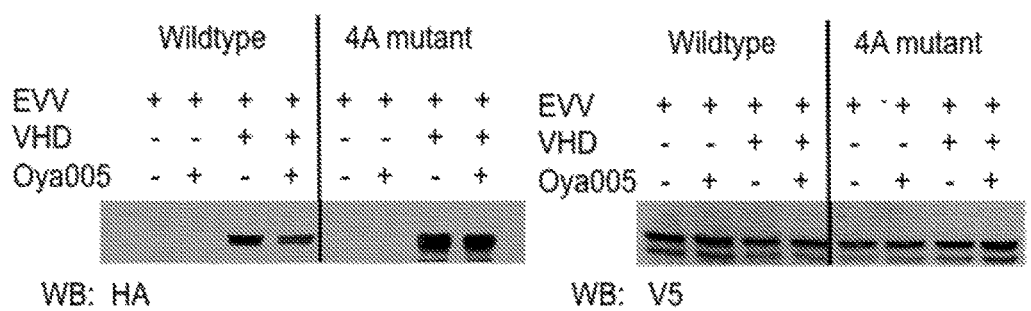
EVV = EGFP-V5-Vif
VHD = Vif-HA-REACh2
Oya005 = Antagonist Peptide
FIG. 5B

*Modifications shown to be less toxic and negative in anti-Topo1 activity*

*Untested*

*Lactam-CPT
(referred to as OYA002-16)*

TOXICITY: Loss of anti-Topo1 activity

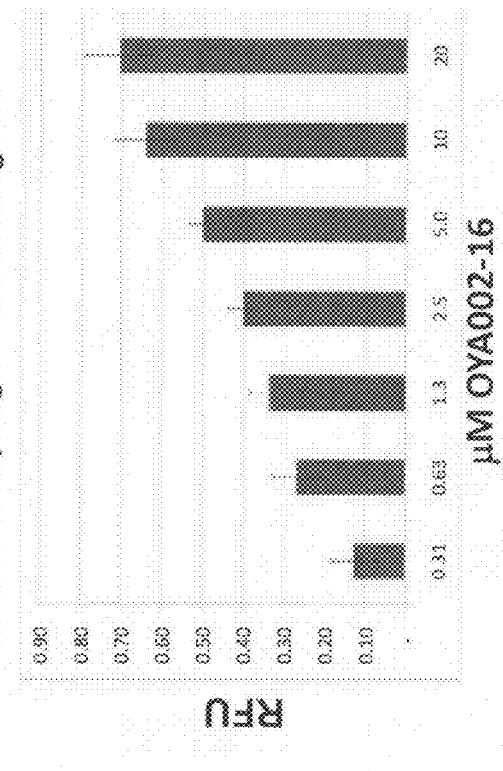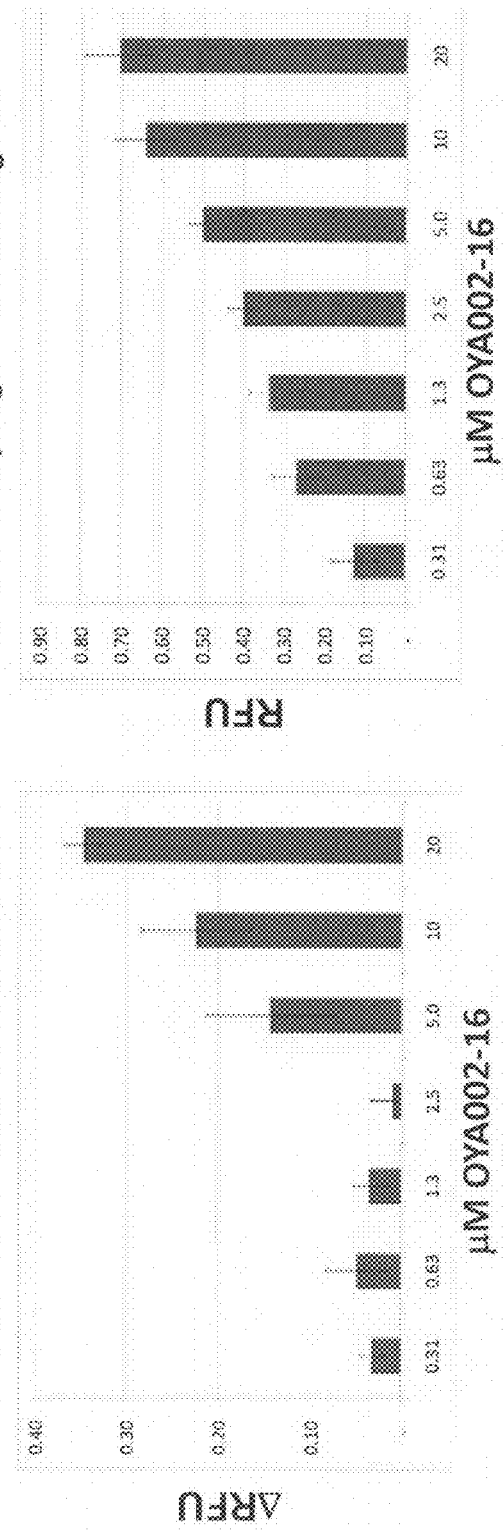
FIG. 11

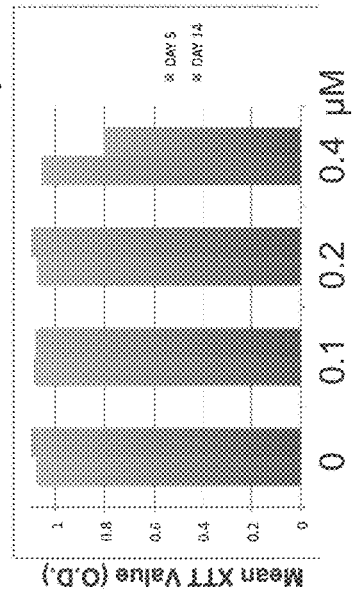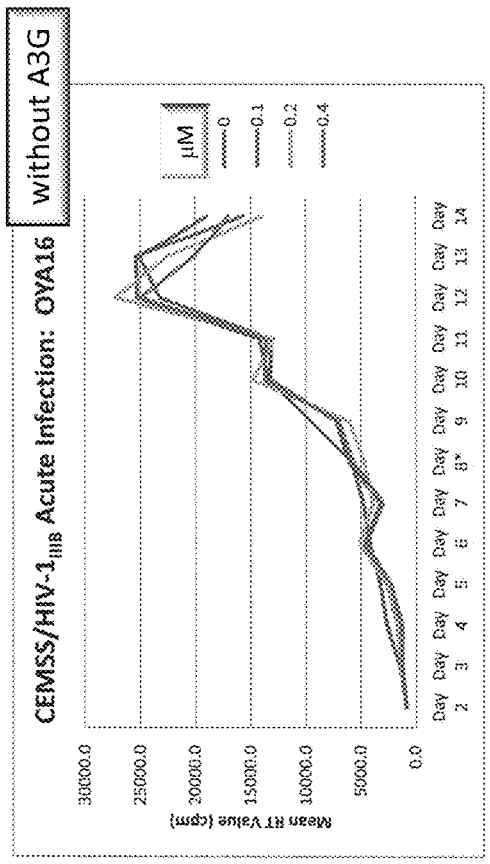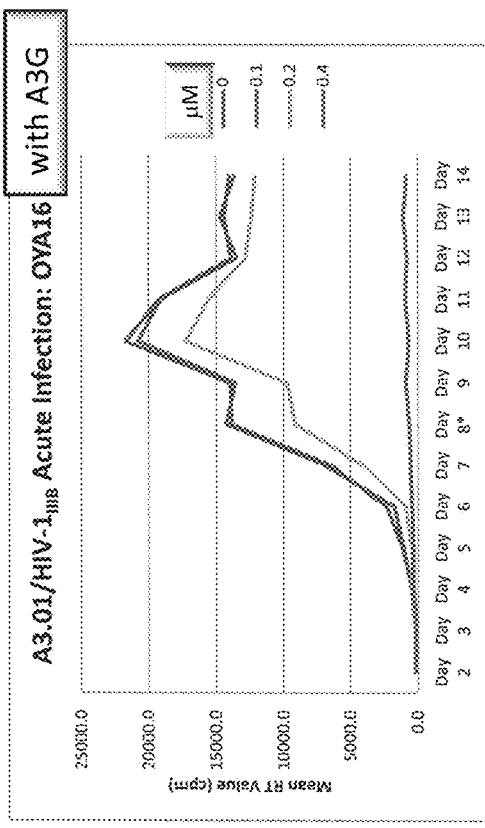
FIG. 15

EFFICACY: OYA002-16 (7 day infections)

| | 50% | ANTIVIRAL INDEX (EC99%) 99% |
|---|---|---|
| 92RW009 (Subtype A) | 42.1 | >314 |
| 93BW016 (Subtype A) | 48.6 | >347 |
| 92US155 (Subtype B) | 55.9 | >335 |
| QZ4589 (Subtype B) | 62.3 | >334 |
| 98IT2013 (Subtype C) | 80.6 | >313 |
| 96USNG031 (Subtype C) | 28.7 | >214 |
| 92UG021 (Subtype D) | 80.3 | >233 |
| 92UG067 (Subtype D) | 4.4 | >297 |
| CMU02 (Subtype E) | 41.8 | >333 |
| CMU08 (Subtype E) | 56.7 | >315 |
| 93BR020 (Subtype F) | 53.3 | >357 |
| 93BR024 (Subtype F) | 57.9 | >323 |
| RU103 (Subtype G) | 40.1 | >327 |
| RU132 (Subtype G) | 44.8 | >184 |
| BCF01 (Group O) | 85.2 | >49.4 |
| BCF02 (Group O) | 15.3 | >280 |
| YBF30 (Group N) | 56.9 | 80% |
| | 50% | |
| A17 | 49.6 | >76 |
| MDR769 | 53.7 | >191 |
| M69R07 | 34.6 | >156 |
| 1022-48 | 41.3 | >215 |
| N(4.3 gp41(36G) Nef

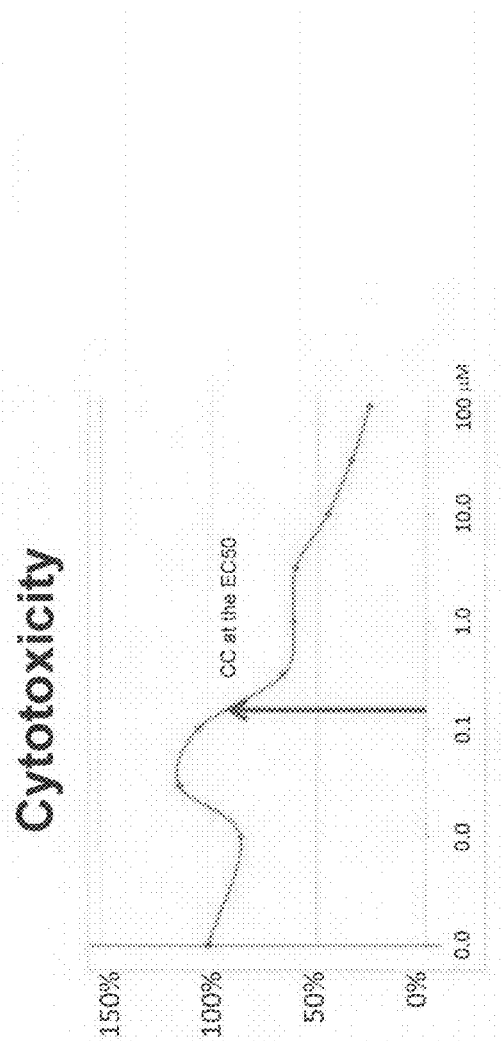

EFFICACY: OYA002-16 and OYA004-06

OYA004-06 structure

| HIV-1 Isolate | Compound | IC50 (uM) | IC90 (uM) | TC50 (uM) | TI (TC50/IC50) |
|---|---|---|---|---|---|
| NL4-3 (Subtype B) | OYA002-16 | 0.27 | 0.09 | 33.3 | 378 |
| | OYA004-06 | 0.93 | 0.44 | >100 | >225 |
| 92RW016 (Subtype A) | OYA002-16 | 0.50 | 0.14 | 33.3 | 237 |
| | OYA004-06 | 0.97 | 0.48 | >100 | >209 |
| 92UG021 (Subtype D) | OYA002-16 | 0.51 | 0.14 | 33.3 | 238 |
| | OYA004-06 | 1.63 | 0.49 | >100 | >203 |
| JV1083 (Subtype G) | OYA002-16 | 0.6 | 0.16 | 33.3 | 214 |
| | OYA004-06 | 1.7 | 0.54 | >100 | >185 |

TOXICITY: Lead Scaffold OYA002-16

Test

| Test | Cell Type | Day 1 | Day 2 | Day 3 |
|---|---|---|---|---|
| Cytostasis | | | | |
| Cell Count | HepG2 | - | - | - |
| Cell Cycle Arrest | HepG2 | - | - | - |
| Mitosis Marker (P-H3) | HepG2 | + | - | +/- |
| Nuclear Size | HepG2 | + | - | - |
| Morphology | Cell Type | 1 | 2 | 3 |
| Cytoskeletal Disruption (Microtubules) | HepG2 | - | - | +/- |
| Mitochondrial Mass | HepG2 | - | - | + |
| Nuclear Size | Rat Hepatocytes | | | |
| Stress and Apoptosis | Cell Type | 1 | 2 | 3 |
| Macromolecular Synthesis | Stimulated PBMCs | | | +/- |
| Stress Kinase Activation (cJun) | HepG2 | +/- | | +/- |
| DNA Damage Response (p53) | HepG2 | +/- | | +/- |
| Oxidative Stress (H2AX) | HepG2 | | | |
| Mitochondrial Potential (TMRE) | HepG2 | | | |
| DNA Fragmentation | Rat Hepatocytes | | | |
| ER stress/DNA Damage (Gadd153) | Rat Hepatocytes | | | |
| Apoptosis (Cytochrome c) | Rat Hepatocytes | | | |
| Phospholipidosis/Lysosomal Mass (Lysotracker Red) | Rat Hepatocytes | | | |
| Mitochondrial Potential (TMRE) | Rat Hepatocytes | | | |
| Steatosis (LipidTox Far Red) | Rat Hepatocytes | | | |
| ROS | Rat Hepatocytes | | | |
| Glutathione | HeLa | - | | |
| APO-ONE Homogeneous Caspase-3/7 | HeLa | | | |
| Cytotox-ONE Homogeneous Membrane Integrity | | | | |

Test

| Test | Cell Type | Day 1 | Day 3 | Day 5 | Day 14 |
|---|---|---|---|---|---|
| Viability | | | | | |
| XTT Assay | Unstimulated PBMCs | | | | |
| XTT Assay | Stimulated PBMCs | | | | |
| XTT Assay | Monocyte-Macrophages | | | | |
| XTT Assay | Dendritic Cells | | | | |
| XTT Assay | Hepatocytes | | | | |
| XTT Assay | iPS Cardiomyocyte | | | | |
| XTT Assay | iPS Neurons | | | | |
| XTT Assay | RPTEC Kidney Cells | | | | |
| CM Colony Formation | Bone Marrow Progenitors | | | | |
| 5 Day Toxicity Assay | Rat Hepatocytes | | | | |
| >80% Cell Loss | HepG2 | - | | | |

AC50 Legend
- ++ = <0.2 μM
- + = 0.2-2 μM
- +/- = 2-40 μM
- - = >40 μM

FIG. 17

STABILITY and SOLUBILITY: OYA002-16

| Client ID | Test Conc. | Species | Mean plasma fraction Unbound | Mean plasma fraction Bound | Recovery | Binding Classification |
|---|---|---|---|---|---|---|
| propranolol | 5μM | mouse | 16.7% | 83.3% | 102% | Moderate Binding |
| warfarin | 5μM | mouse | 8.0% | 92.0% | 84.9% | Control Binding |
| BRD25 | 5μM | mouse | 3.5% | 96.5% | 88.2% | |
| O2_16 | 5μM | mouse | 26.9% | 73.1% | 77.3% | |

FIG. 18

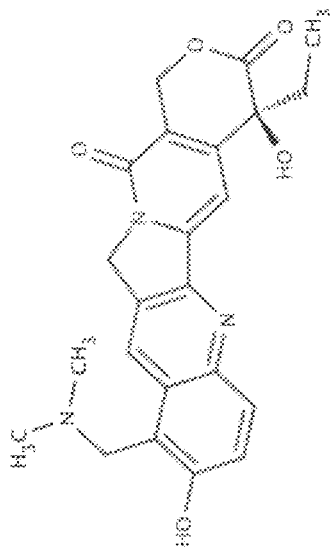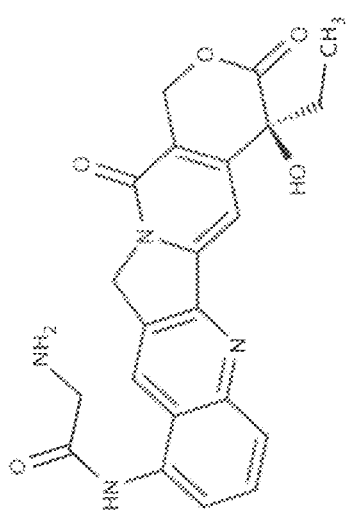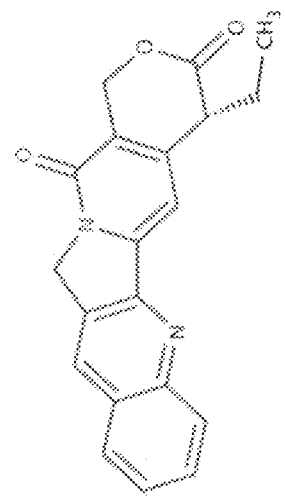
FIG. 20B

CAMPTOTHECIN DERIVATIVES AS ANTI-HIV AGENTS AND METHODS OF IDENTIFYING AGENTS THAT DISRUPT VIF SELF-ASSOCIATION

CROSS-REFERENCE TO RELATED APPLICATIONS

This application is a U.S. National Phase filing under 35 U.S.C. § 371 of International Application No. PCT/US2014/043974, filed Jun. 24, 2014, and published as WO 2014/210082-A2 on Dec. 31, 2014, which claims priority benefit of U.S. Provisional Patent Application Ser. No. 61/838,574, filed Jun. 24, 2013. The entire contents of each of the prior applications are incorporated herein by reference in their entirety.

GOVERNMENT RIGHTS STATEMENT

The present invention was made with U.S. Government support under National Institutes of Health Grant No. R21NS067671-01. The U.S. Government has certain rights in the invention.

FIELD OF THE INVENTION

The present invention relates to the use of camptothecin derivatives as anti-HIV agents that disrupt self-association of the viral infectivity factor (Vif) found in HIV and other retroviruses. The present invention also relates to methods of identifying agents that disrupt VIf self-association and methods of using these agents, including methods of treating or preventing HIV infection.

BACKGROUND OF THE INVENTION

HIV-1 is the causative agent of AIDS and presently infects approximately 33 million persons worldwide with approximately 1.9 million infected persons in North America alone. Recent studies have shown that HIV/AIDS has become a global epidemic that is not under control in developing nations. The rapid emergence of drug-resistant strains of HIV throughout the world has placed a priority on innovative approaches for the identification of novel drug targets that may lead to a new class of anti-retroviral therapies.

The virus contains a 10-kb single-stranded RNA genome that encodes three major classes of gene products that include: (i) structural proteins (Gag, Pol and Env); (ii) essential trans-acting proteins (Tat, Rev); and (iii) "auxiliary" proteins that are not required for efficient virus replication in permissive cells (Vpr, Vif, Vpu, Nef) [reviewed in (1)]. There has been a heightened interest in Vif as an antiviral target because of the discovery that the primary function of Vif is to overcome the action of a cellular antiviral protein known as APOBEC3G or A3G (2).

In 1984, it was determined that HIV was the virus that causes AIDS and researchers declared that a vaccine would be available within two years. Nearly three decades later, there is still no vaccine available and the primary focus remains on developing therapeutics for those already infected. Currently, the primary HIV preventative is the combination treatment known as STRIBILD™. This medication contains 3 components of the highly active anti-retroviral therapy (HAART) regimen (i.e., one integrase (IN) and two reverse transcriptase (RT) inhibitors). However, HIV strains with resistance to some or all of these components had already emerged prior to the availability of STRIBILD™, thus rendering it ineffective against such strains. Furthermore, not only has HIV developed resistance to STRIBILD™ components, but it also has developed resistance to all HAART medications to date, including inhibitors of all HIV enzymatic and viral entry targets. In fact, it is common to see drug resistance even among treatment-naïve individuals worldwide, emphasizing that at least some of the current drugs have limited efficacy in a subset of untreated, infected individuals. The barrier to developing resistance to HIV drugs is low and often a single codon change in the targeted protein is sufficient to cause resistance to more than one inhibitor of the same class (i.e., M46I/L/V in the HIV protease confers resistance to 7 out of 8 inhibitors). The ever-present problem of drug resistance together with the lack of success in developing a vaccine accentuate the need for novel HIV prevention and treatment strategies that are unlikely to develop resistance.

The present invention is directed toward overcoming these and other deficiencies in the art.

SUMMARY OF THE INVENTION

The present invention is based, in part, on the discovery that identifying agents that disrupt Vif self-association can lead to the identification of novel agents for use as anti-HIV therapeutics.

In one aspect, the present invention provides compounds that are effective as inhibitors or disruptors of Vif self-association. The present invention further relates to various uses of these compounds.

The present invention also provides a high throughput primary screen for small molecules and other agents that have Vif multimerization antagonist activity. In one embodiment, this HTS primary screen is based on a live cell quenched fluorescence resonance energy transfer (FRET) assay.

In a more particular embodiment, the present invention provides a homogeneous assay based on the expression of fluorescent protein chimeras of Vif in HEK 293T cells to achieve distance-dependent quenching through FRET mediated by Vif multimerization. Compounds that disrupt Vif multimerization will yield an enhanced fluorescence signal. Hits from the primary screen can then be subjected to an orthogonal secondary screen (e.g., in *Escherichia coli*). Hits from the secondary screen can then be validated for their (1) antiviral activity through infectivity assays; (2) ability to inhibit co-immunoprecipitation of differentially epitope tagged Vif; and (3) ability to protect APOBEC3G from Vif-dependent degradation.

Compounds identified using the assays of the present invention can be used as lead compounds to address a mandate for novel therapeutics and also provide new research reagents to study the structure and function of Vif.

The present invention also provides a method of treating or preventing HIV infection or AIDS in a patient using anti-HIV agents identified using the assay of the present invention. Further aspects and embodiments are described in more detail herein below.

In one aspect, the present invention addresses the deficiency in the art of effective assays for identifying small molecules that disrupt Vif dimerization and, therefore, have anti-HIV activity.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3 is a graph illustrating that Vif dimerization antagonist peptides suppress HIV-1 infectivity. MT2 cells grown in microtiter dishes were infected with live HIV-1 virus at 0.01 MOI and treated every other day with either AZT (1 μM), Control peptide (50 μM), Peptide 1 (50 μM) or Peptide 2 (50 μM) or left untreated (viral control). At the indicated days post-infection, cells were harvested for cell lysate preparation and reverse transcriptase quantification. Lysates were prepared from parallel cultures of uninfected and untreated cells (cell control) as controls for the reverse transcriptase assays.

FIG. 4 are schematics illustrating an antiviral strategy that involves disrupting Vif dimerization. The left schematic illustrates HIV life cycle enabled with Vif dimer formed. The right schematic illustrates A3G host-defense enabled without Vif dimer.

FIG. 5B are photographs (top panels) and Western blots (bottom panels) illustrating in-cell high throughput screen for Vif dimerization antagonists.

FIG. 11 are graphs showing results from a primary screen (left side) and a secondary screen (right side) of the OYA002-16 small molecule scaffold.

FIG. 15 illustrates graphs showing results relating to efficacy studies of lead scaffold OYA002-16.

FIGS. 16A-1, 16A-2, 16A-3, 16A-4 are graphs showing results of efficacy studies with regard to OYA002-16.

FIGS. 16B-1 and 16B-2 are graphs and illustrations showing results of efficacy studies with regard to OYA002-16 and OYA004-06.

FIG. 17 is a graph showing results of toxicity studies relating to lead scaffold OYA002-16.

FIG. 18 is a graph showing results of stability and solubility studies relating to lead scaffold OYA002-16.

FIGS. 20A-1 and 20A-2 illustrate lead optimization goals for improving solubility and decreasing toxicity with respect to a Vif inhibitor of the present disclosure.

FIG. 20B illustrate lead optimization goals for improving solubility and decreasing toxicity with respect to a Vif inhibitor of the present disclosure.

DETAILED DESCRIPTION OF THE INVENTION

The present invention is based, in part, on the discovery that disrupting self-association of the HIV viral infectivity factor (Vif) can be a mechanism for use in identifying agents that can be used as anti-HIV agents.

Vif binds to and induces the destruction of APOBEC3G (also referred to herein as "A3G"), which is a broad antiviral host-defense factor. Therefore, Vif is essential for HIV infection. Vif subunits interact to form multimers and this property has been shown to be necessary for HIV infectivity. The segment of Vif that mediates subunit interaction was previously determined to be proline-proline-leucine-proline (PPLP). However, to date, there has not been an effective high throughput screening (HTS) assay to identify agents that disrupt Vif self-association. The present invention is effective to address this need.

Figure 1:
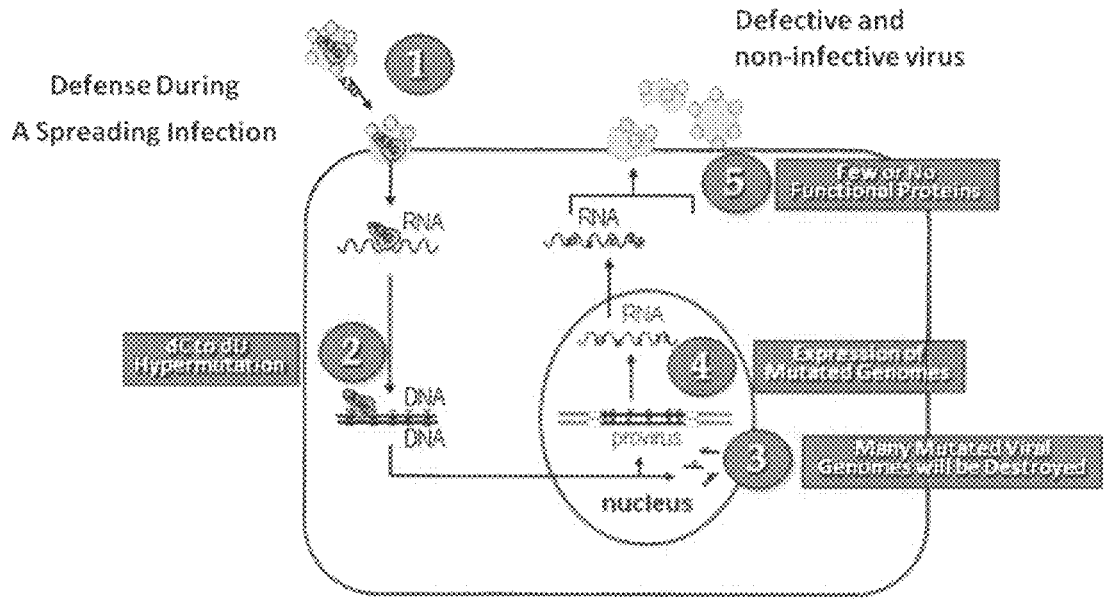
FIG. 1 is a schematic illustrating how A3G can integrate with viral particles and inhibit viral replication when Vif is disabled.

As shown in FIG. 1, A3G can integrate with viral particles and inhibit viral replication when Vif is disabled. For example, as shown in FIG. 1: Part 1: In the absence of a functional Vif A3G is incorporated into viral particles and is bound to viral RNA upon release of the viral proteins into the target cell. Part 2: During reverse transcription of the viral RNA into proviral DNA A3G causes dC to dU hyper-mutations (X) on the viral minus strand that is single-stranded in the small window of time before the positive strand is synthesized. Part 3: Mutated proviral DNA is either degraded by DNA repair machinery recognizing dU in DNA or incorporated into the host genome with dG to dA mutations in the positive strand since reverse transcriptase reads the dU mutations as needing a dA complementary nucleotide instead of a dG. Part 4: The virus uses the host cell machinery to make mutated viral RNA and proteins; the mutations cause missense and stop codons that are catastrophic for viral function. Part 5: Thus, the progeny virions are defective and non-infective.

Figure 2:
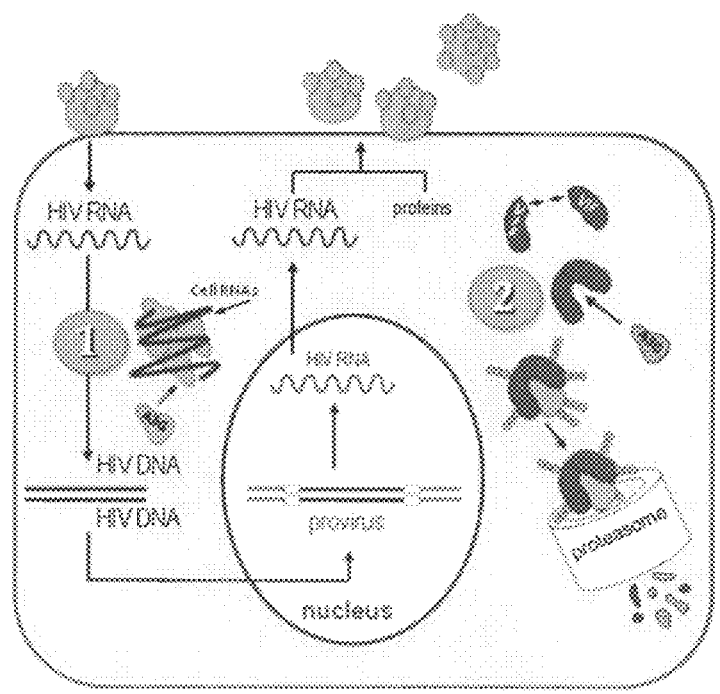
FIG. 2 is a schematic illustrating how HIV evades A3G twice during infection.

As shown in FIG. 2, HIV evades A3G twice during infection. For example, as shown in FIG. 2, HIV Ssuppresses A3G host defense activity in permissive cells by: (1)

Early Block: HIV infection induces A3G inactivation through complex formation with host cell RNAs. (2) Late Block: Vif is expressed and Vif dimers bind to A3G to direct its destruction before A3G can be packaged with virions.

Inhibitors of Vif Self-Association

In one aspect, the present invention provides small molecule compounds that are inhibitors of Vif self-association (also referred to generally herein as "Vif inhibitors").

Vif binds to and induces the destruction of APOBEC3G (also referred to herein as "A3G"), which is a broad antiviral host-defense factor. Therefore, Vif is essential for HIV infection. Vif subunits interact to form multimers and this property has been shown to be necessary for HIV infectivity. The segment of Vif that mediates subunit interaction was previously determined to be proline-proline-leucine-proline (PPLP) (see FIG. 3). As shown in FIG. 3, its has been confirmed and established that the antiviral activity of VDA peptides were dependent on Vif and A3G for highest efficacy (JH Miller et al., *Retrovirology* 2007). In various embodiments, small molecule compounds or other agents that disrupt Vif self-association (also referred to herein as "Vif dimerization" or "Vif multimerization") are suitable as Vif inhibitors in accordance with the present invention. As shown in FIG. 4, as provided by the present disclosure, one antiviral strategy aginst HIV is to disrupt Vif dimerization.

In one embodiment, the Vif inhibitor of the present invention is effective to inhibit Vif dimerization by direct or indirect inhibition of binding of Vif dimers at the Vif dimerization domain, said Vif dimerization domain comprising the amino acid sequence of proline-proline-leucine-proline (PPLP). In another embodiment, the Vif inhibitor of the present invention is effective to inhibit Vif from binding to A3G. In another embodiment, the Vif inhibitor of the present invention is effective to inhibit Vif-dependent degradation of A3G. In another embodiment, the Vif inhibitor of the present invention is effective to inhibit Vif-dependent degradation of A3G by inhibiting interaction of Vif with one or more enzymes selected from the group consisting of Cullin 5, Elongin B, and Elongin C, thereby inhibiting ubiquitination of A3G.

Vif inhibitors for use in the methods of the present disclosure are as disclosed herein.

In certain embodiments, the present invention provides camptothecin derivatives as small molecule compounds that were identified using the screening assay of the present invention. The small molecule compounds are effective as inhibitors of Vif self-association.

In certain embodiments, the Vif inhibitor of the present invention can include, without limitation, camptotechin, topotecan, irinotecan, and analogs thereof and those having a related chemical scaffold (chemotype) thereof. Certain camptothecin derivatives for use as Vif inhibitors of the present disclosure are illustrated by chemical structure in FIGS. 7, 8, 16B-2, 20A-1, 20B, 21A, and 21B hereof.

In one aspect, the present invention provides a compound of formula (I):

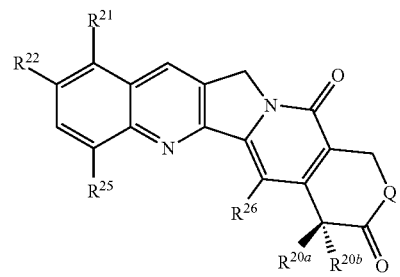

(I)

or a pharmaceutically acceptable salt thereof, wherein:
Q is selected from NH, O, and S;
$R^{20a}$ and $R^{20b}$ are individually selected from hydrogen, hydroxy, and $C_{1-6}$alkyl;
$R^{21}$ is selected from hydrogen, —NHC(=O)$(CH_2)_p$NR$^{23}$R$^{24}$, and —$(CH_2)_p$NR$^{23}$R$^{24}$;
p is 0, 1, 2, 3, or 4;
$R^{22}$ is selected from hydrogen and hydroxyl;
$R^{23}$ and $R^{24}$ are individually selected from hydrogen and $C_{1-6}$ alkyl; and
$R^{25}$ and $R^{26}$ are individually selected from hydrogen and —$NO_2$.

In one sub-group of compounds, Q is O.
In one sub-group of compounds, Q is selected from NH and S.
In a particular sub-group of compounds, Q is NH.
In another particular sub-group of compounds, Q is S.
In one sub-group of compounds, $R^{20a}$ is $C_{1-6}$ alkyl.
In one sub-group of compounds, $R^{20a}$ and $R^{20b}$ are individually selected from hydrogen, hydroxy, methyl, and ethyl.
In one sub-group of compounds $R^{20a}$ is selected from hydrogen and hydroxy.
In a particular sub-group of compounds, $R^{20a}$ is hydrogen.
In another particular sub-group of compounds, $R^{20a}$ is hydroxy.
In one sub-group of compounds $R^{20b}$ is $C_{1-6}$alkyl.
In one sub-group of compounds $R^{20b}$ is hydrogen.
In a particular sub-group of compounds, $R^{20b}$ is ethyl.
In one sub-group of compounds, $R^{20a}$ is hydrogen or hydroxy and $R^{20b}$ is ethyl.
In a particular sub-group of compounds, $R^{20a}$ is hydrogen and $R^{20b}$ is ethyl.
In a particular sub-group of compounds, $R^{20a}$ is hydroxy and $R^{20b}$ is ethyl.
In one sub-group of compounds, $R^{21}$ is hydrogen.
In another sub-group of compounds, $R^{21}$ is —NHC(=O)$(CH_2)_p$NR$^{23}$R$^{24}$ (e.g., —NHC(=O)$CH_2$NR$^{23}$R$^{24}$, such as —NHC(=O)$CH_2$NH$_2$).
In another sub-group of compounds, $R^{21}$ is —$(CH_2)_p$NR$^{23}$R$^{24}$ (e.g., $CH_2$N$(CH_3)_2$).
In one subgroup of compounds, p is 1, 2, 3, or 4. In a particular subgroup, p is 1 or 2. In a more particular subgroup, p is 1.
In one subgroup of compounds, $R^{22}$ is hydrogen.
In one subgroup of compounds, $R^{22}$ is hydroxyl.
In one subgroup, $R^{23}$ and $R^{24}$ are individually selected from hydrogen and methyl.
In one subgroup of compounds, $R^{25}$ and $R^{26}$ are both hydrogen.
In one subgroup of compounds, $R^{25}$ and $R^{26}$ are both —$NO_2$.

In particular embodiments, a suitable Vif inhibitor of formula (I) is a compound selected from the group consisting of

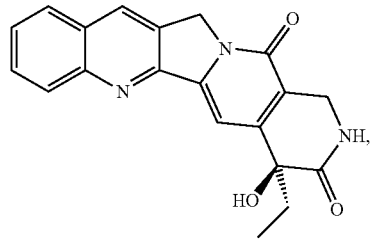
(I-a)

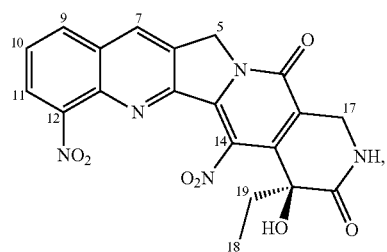
(I-b)

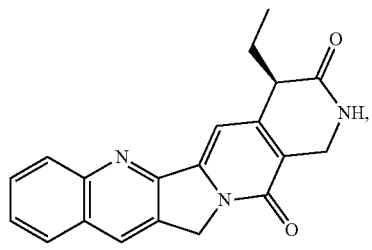
(I-c)

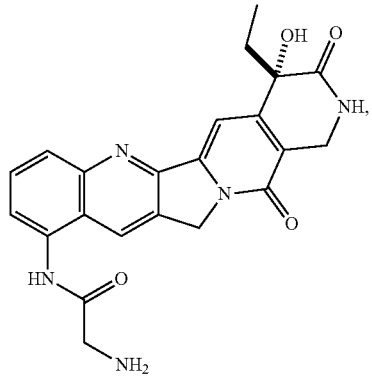
(I-d)

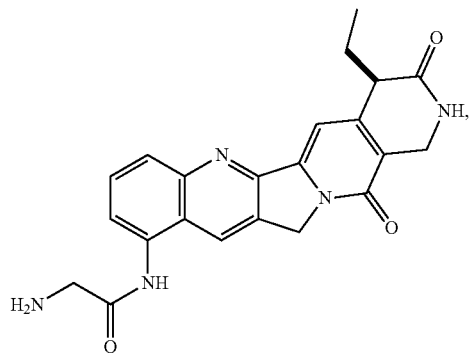
(I-e)

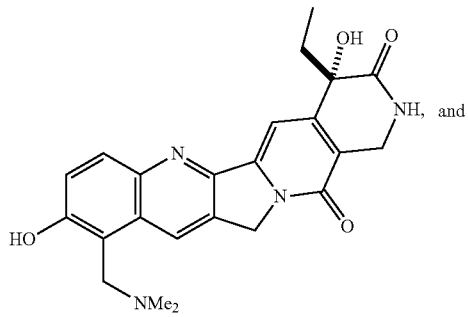
(I-f)

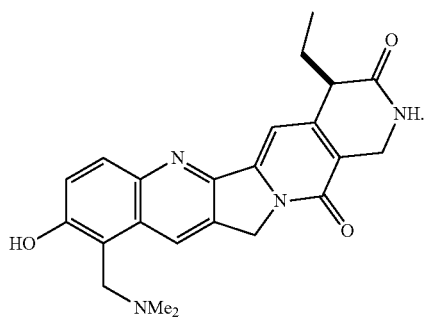
(I-g)

The compound of formula (I-a) is also referred to herein as "OYA-002-16" or "OYA002-16." The compound of formula (I-b) is also referred to herein as "OYA-004-006" or "OYA004-006." The compound of formula (I-c) is also referred to herein as deoxycamptothecin lactam (denoted as formula 2 in the figure). The compound of formula (I-d) is also referred to herein as 9-glycinamido camptothecin lactam (denoted as formula 5 in the figure). The compound of formula (I-e) is also referred to herein as 9-glycinamido deoxycamptothecin lactam (denoted as formula 7 in the figure). The compound of formula (I-f) is also referred to herein as topotecan lactam (denoted as formula 9 in the figure). The compound of formula (I-g) is also referred to herein as and deoxytopotecan lactam (denoted as formula 10 in the figure).

The Vif inhibitor compounds for use in the methods of the present invention can include functional derivatives of any of the Vif inhibitor compounds disclosed herein, and pharmaceutically acceptable salts thereof.

In another aspect, the present invention provides pharmaceutical compositions comprising a compound of Formula (I).

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, which are herein incorporated by reference in their entirety.

Unless otherwise specified, alkyl is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. Hydrocarbon refers to any substituent comprised of hydrogen and carbon as the only elemental constituents.

An "alkenyl" group refers to an unsaturated hydrocarbon group containing at least one carbon-carbon double bond, including straight-chain, branched-chain, and cyclic groups. Preferably, the alkenyl group has 1 to 12 carbons. More preferably it is a lower alkenyl of from 1 to 7 carbons. The alkenyl group may be substituted or unsubstituted. When substituted, the substituted group(s) is preferably hydroxyl, cyano, alkoxy, =O, =S, $NO_2$, $N(CH_3)_2$, halogen, amino, or SH.

An "alkynyl" group refers to an unsaturated hydrocarbon group containing at least one carbon-carbon triple bond, including straight-chain, branched chain, and cyclic groups. Preferably, the alkynyl group has 1 to 12 carbons. More preferably it is a lower alkynyl of from 1 to 7 carbons. The alkynyl group may be substituted or unsubstituted. When substituted, the substituted group(s) is preferably hydroxyl, cyano, alkoxy, =O, =S, $NO_2$, $N(CH_3)_2$, amino, or SH.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The abbreviations Me, Et, Ph, Tf, Ts and Ms represent methyl, ethyl, phenyl, trifluoromethanesulfonyl, toluenesulfonyl and methanesulfonyl, respectively. A comprehensive list of abbreviations utilized by organic chemists (i.e., persons of ordinary skill in the art) appears in the first issue of each volume of the Journal of Organic Chemistry. The list, which is typically presented in a table entitled "Standard List of Abbreviations" is incorporated herein by reference.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Alkoxy or alkoxyl refers to groups of from 1 to 8 carbon atoms of a straight, branched or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purpose of this application, alkoxy and lower alkoxy include methylenedioxy and ethylenedioxy. A particular subgroup of alkoxy is $C_1$ alkoxy, which refers to alkoxy having 1, 2, 3, 4, 5, or 6 carbon atoms.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons. The double bonded oxygen, when referred to as a substituent itself is called "oxo".

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloalkyl or aryl carbocycle residue in which from one to three carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

The term "heterocyclic group" includes within its scope aromatic, non-aromatic, unsaturated, partially saturated and fully saturated heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. A particular non-limiting example is a morpholinyl group.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

Substituents R″ are generally defined when introduced and retain that definition throughout the specification and in all independent claims.

As used herein, and as would be understood by the person of skill in the art, the recitation of "a compound"—unless expressly further limited—is intended to include salts, solvates and inclusion complexes of that compound. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in *Remington: The Science and Practice of Pharmacy* 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

While it may be possible for the compounds of the invention to be administered as the raw chemical, it is preferable to present them as a pharmaceutical composition. According to a further aspect, the present invention provides a pharmaceutical composition comprising a compound of the invention or a pharmaceutically acceptable salt or solvate thereof, together with one or more pharmaceutical carriers thereof and optionally one or more other therapeutic ingredients. The carrier(s) must be "acceptable" in the sense of being compatible with the other ingredients of the formulation and not deleterious to the recipient thereof.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of the present invention, as well as salts, solvates, and physiological functional derivatives thereof, may be administered as the raw chemical. Additionally, the active ingredient may be presented as a pharmaceutical composition.

Pharmaceutical compositions of the present invention comprise an effective amount of one or more compound of the present invention, or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one compound of the present invention, or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The term "lentivirus" as used herein may be any of a variety of members of this genus of viruses. The lentivirus may be, e.g., one that infects a mammal, such as a sheep, goat, horse, cow or primate, including human. Typical such viruses include, e.g., Vizna virus (which infects sheep); simian immunodeficiency virus (SIV), bovine immunodeficiency virus (BIV), chimeric simian/human immunodeficiency virus (SHIV), feline immunodeficiency virus (FIV) and human immunodeficiency virus (HIV). "HIV," as used herein, refers to both HIV-1 and HIV-2. Much of the discussion herein is directed to HIV or HIV-1; however, it is to be understood that other suitable lentiviruses are also included.

The term "mammal" as used herein refers to any non-human mammal. Such mammals are, for example, rodents, non-human primates, sheep, dogs, cows, and pigs. The preferred non-human mammals are selected from the rodent family including rat and mouse, more preferably mouse. The preferred mammal is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids which can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptide, homodimers, heterodimers, variants of polypeptides, modified polypeptides, derivatives, analogs, fusion proteins, among others. The polypeptides include natural peptides, recombinant peptides, synthetic peptides, or a combination thereof.

"Pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

As used herein, "pharmaceutical compositions" include formulations for human and veterinary use.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

"Viral infectivity" as that term is used herein means any of the infection of a cell, the replication of a virus therein, and the production of progeny virions therefrom.

A "virion" is a complete viral particle; nucleic acid and capsid, further including and a lipid envelope in the case of some viruses.

Methods of Using the Inhibitors of Vif Self-Association

The inhibitors of Vif self-association described herein can be used for various uses.

In one embodiment, the inhibitors of Vif self-association described herein can be used in a method for treating or preventing HIV infection or AIDS in a patient. This method involves administering to a patient in need of such treatment or prevention a therapeutically effective amount of a compound of described herein, or a pharmaceutically acceptable salt thereof. The method can further include administering a therapeutically effective amount of at least one other agent for treating HIV selected from the group consisting of HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

In one embodiment, the inhibitors of Vif self-association described herein can be used in a method for inhibiting infectivity of a lentivirus in a cell. This method involves contacting a cell with an antiviral-effective amount of a compound described herein, or a pharmaceutically acceptable salt thereof.

In one embodiment, the inhibitors of Vif self-association described herein can be used in a method for inhibiting Vif self-association in a cell. This method involves contacting a cell with an inhibitory-effective amount of a compound described herein, or a pharmaceutically acceptable salt thereof.

The present invention further provides various methods of using the Vif self-association inhibitors, where the first step involves conducting the screening assay of the present invention to identify the agents as being inhibitors of Vif self-association. Such methods are described below.

In one embodiment, the present invention provides a method for inhibiting infectivity of a lentivirus. This method involves identifying an agent that disrupts Vif self-association by performing the screening method of the present invention, and contacting a cell with an antiviral-effective amount of said agent under conditions effective to disrupt or inhibit multimerization of Vif in the cell, thereby inhibiting infectivity of the lentivirus. In one embodiment, the agent is effective to inhibit dimerization by direct or indirect inhibition of binding of Vif dimmers at the Vif dimerization domain, said Vif dimerization domain comprising the amino acid sequence of proline-proline-leucine-proline (PPLP).

In one embodiment, the present invention provides a method for inhibiting Vif self-association in a cell. This method involves identifying an agent that disrupts Vif self-association by performing the screening method of the present invention, and then contacting a cell with an inhibitory-effective amount of said agent under conditions effective to disrupt or inhibit multimerization of Vif in the cell, thereby inhibiting Vif self-association in the cell.

In one embodiment, the present invention provides a method for treating or preventing HIV infection or AIDS in a patient. This method involves identifying an agent that disrupts Vif self-association by performing the screening method of the present invention, and then administering to a patient in need of such treatment or prevention a therapeutically effective amount of the agent.

Methods of Treatment

In one embodiment, the present invention provides methods of treating a disease, disorder, or condition associated with a viral infection. Preferably, the viral infection is HIV. The method comprises administering to a subject, such as a mammal, preferably a human, a therapeutically effective amount of a pharmaceutical composition that inhibits Vif self-association.

The invention includes compounds identified using the screening methods discussed elsewhere herein. Such a compound can be used as a therapeutic to treat an HIV infection or otherwise a disorder associated with the inability to dissociate Vif:Vif complexes.

The ability for a compound to inhibit Vif self-association can provide a therapeutic to protect or otherwise prevent viral infection, for example HIV infection.

Thus, the invention includes pharmaceutical compositions. Pharmaceutically acceptable carriers that are useful include, but are not limited to, glycerol, water, saline, ethanol and other pharmaceutically acceptable salt solutions such as phosphates and salts of organic acids. Examples of these and other pharmaceutically acceptable carriers are described in *Remington's Pharmaceutical Sciences* (1991, Mack Publication Co., N.J.), the disclosure of which is incorporated by reference as if set forth in its entirety herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic peritoneally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, peritoneal, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, peritoneal, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

As used herein, "peritoneal administration" of a pharmaceutical composition includes any route of administration characterized by physical breaching of a tissue of a subject and administration of the pharmaceutical composition through the breach in the tissue. Peritoneal administration thus includes, but is not limited to, administration of a pharmaceutical composition by injection of the composition, by application of the composition through a surgical incision, by application of the composition through a tissue-penetrating non-surgical wound, and the like. In particular, peritoneal administration is contemplated to include, but is not limited to, subcutaneous, intraperitoneal, intramuscular, intrasternal injection, and kidney dialytic infusion techniques.

A pharmaceutical composition can consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Controlled- or sustained-release formulations of a pharmaceutical composition of the invention may be made using conventional technology.

Formulations of a pharmaceutical composition suitable for peritoneal administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for peritoneal administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for peritoneal administration, the active ingredient is provided in dry (i.e., powder or granular) form for reconstitution with a suitable vehicle (e.g., sterile pyrogen-free water) prior to peritoneal administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic peritoneally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, and the like. Preferably, the compound is, but need not be, administered as a bolus injection that provides lasting effects for at least one day following injection. The bolus injection can be provided intraperitoneally.

Method of Screening

The current invention relates to a method of screening for an agent (e.g., a small molecule compound) that disrupts Vif self-association (also referred to herein as Vif dimerization and Vif multimerization).

In one aspect, the present invention provides a method of identifying an agent that disrupts Vif self-association. This method involves (i) providing a Vif:Vif complex comprising a first Vif protein or fragment associated with a second Vif protein or fragment; (ii) contacting the Vif: if complex with a test agent under conditions effective to generate a detectable signal when the Vif:Vif complex is disrupted; and (iii) detecting the detectable signal to determine whether or not the test agent disrupts the Vif:Vif complex, wherein disruption of the Vif:Vif complex by the test agent identifies an agent that disrupts Vif self-association.

A suitable test agent can include a small molecule, a peptide, a polypeptide, an oligosaccharide, a polysaccharide, a polynucleotide, a lipid, a phospholipid, a fatty acid, a steroid, an amino acid analog, and the like. In one embodiment, the test agent is from a library of small molecule compounds.

In one embodiment, the contacting step comprises incubating the Vif:Vif complex with one type of test agent or more than one type of test agent.

In another embodiment, the contacting step comprises associating the test agent with the Vif:Vif complex either directly or indirectly.

The detactable signal may be detected using a detection technique selected from the group consisting of fluorimetry, microscopy, spectrophotometry, computer-aided visualization, and the like, or combinations thereof.

The detectable signal may be selected from the group consisting of a fluorescent signal, a phosphorescent signal, a luminescent signal, an absorbent signal, and a chromogenic signal.

In one embodiment, the fluorescent signal is detectable by its fluorescence properties selected from the group consisting of fluorescence resonance energy transfer (FRET), fluorescence emission intensity, and fluorescence lifetime (FL).

In one embodiment, the Vif:Vif complex is provided with a first detection moiety attached to the first Vif protein or fragment and a second detection moiety attached to the second Vif protein or fragment.

In one embodiment, the first detection moiety and the second detection moiety generate a detectable signal in a distance-dependent manner, so that disruption of the Vif:Vif complex is sufficient to separate the first detection moiety and the second detection moiety a distance effective to generate the detectable signal.

In one embodiment, the first detection moiety and the second detection moiety comprise a fluorescence resonance energy transfer (FRET) pair, wherein the first detection moiety is a FRET donor and the second detection moiety is a FRET acceptor. The FRET donor and the FRET acceptor can comprise a fluorophore pair selected from the group consisting of EGFP-REACh2, GFP-YFP, EGFP-YFP, GFP-REACh2, CFP-YFP, CFP-dsRED, BFP-GFP, GFP or YFP-dsRED, Cy3-Cy5, Alexa488-Alexa555, Alexa488-Cy3, FITC-Rhodamine (TRITC), YFP-TRITC or Cy3, and the like.

In one embodiment, the Vif:Vif complex is provided in a host cell co-transfected with a first plasmid encoding the first Vif protein or fragment and a second plasmid encoding the second Vif protein or fragment.

In one embodiment, the ratio of the first plasmid to the second plasmid is effective to optimize the generation of the detectable signal when the Vif:Vif complex is disrupted. The optimized ratio of the first plasmid to the second plasmid may be about 1:4, wherein the first plasmid further comprises a signal donor moiety and the second plasmid further comprises a signal quencher moiety.

In one embodiment, the host cell is stably or transiently co-transfected with the first and second plasmids.

In one embodiment, the host cell is selected from the group consisting of a mammalian cell, an insect cell, a bacterial cell, and a fungal cell. A suitable mammalian cell can include a human cell.

In one embodiment, the host cell is a cell culture comprising a cell line that is stably co-transfected with the first and second plasmids.

The method of identifying an agent that disrupts Vif self-association of the present invention can be configured as a high throughput screening assay. The high throughput screening assay can have a Z'-factor of between about 0.5 and about 1.0.

The method of identifying an agent that disrupts Vif self-association of the present invention can further involve (i) quantitating the detectable signal; (ii) amplifying the detectable signal; and (iii) attaching a first epitope tag to the first Vif protein or fragment and attaching a second epitope tag to the second Vif protein or fragment, wherein said first and second epitope tags are different from one another.

In one embodiment, the first and second epitope tags are selected from the group consisting of AU1 epitope tags, AU5 epitope tags, Beta-galactosidase epitope tags, c-Myc epitope tags, ECS epitope tags, GST epitope tags, Histidine epitope tags, V5 epitope tags, GFP epitope tags, HA epitope tags, and the like.

The method of identifying an agent that disrupts Vif self-association of the present invention can further involve subjecting the test agent identified as disrupting the Vif:Vif complex to a validation assay effective to confirm disruption of Vif self-association by the test agents.

The method of identifying an agent that disrupts Vif self-association of the present invention can further involve subjecting the test agent identified as disrupting the Vif:Vif complex to toxicity, permeability, and/or solubility assays.

Other methods, as well as variation of the methods disclosed herein will be apparent from the description of this invention. For example, the test compound may be either fixed or increased, a plurality of compounds or proteins may be tested at a single time.

Based on the disclosure presented herein, the screening method of the invention is applicable to a robust Förster quenched resonance energy transfer (FqRET) assay for high-throughput compound library screening in microtiter plates. The assay is based on selective placement of chromoproteins or chromophores that allow reporting on Vif:Vif complex disruption. For example, an appropriately positioned FRET donor and FRET quencher will results in a "dark" signal when the quaternary complex is formed between Vif dimers, and a "light" signal when the Vif:Vif complex is disrupted.

The skilled artisan would also appreciate, in view of the disclosure provided herein, that standard binding assays known in the art, or those to be developed in the future, can be used to assess the disruption of Vif self-association in the presence or absence of the test compound to identify a useful compound. Thus, the invention includes any compound identified using this method.

The screening method includes contacting a mixture comprising recombinant Vif dimers with a test compound and detecting the presence of the Vif:Vif complex, where a decrease in the level of Vif:Vif complex compared to the amount in the absence of the test compound or a control indicates that the test compound is able to inhibit Vif self-association. In certain embodiments, the control is the same assay performed with the test compound at a different concentration (e.g. a lower concentration), or in the absence of the test agent, etc.

Determining the ability of the test compound to interfere with the formation of the Vif:Vif complex, can be accomplished, for example, by coupling the Vif dimers with a tag, radioisotope, or enzymatic label such that the Vif:Vif complex can be measured by detecting the labeled component in the complex. For example, a component of the complex (e.g., a single Vif protein) can be labeled with $^{32}$P, $^{125}$I, $^{35}$S, $^{14}$C, or $^{3}$H, either directly or indirectly, and the radioisotope detected by direct counting of radioemission or by scintillation counting. Alternatively, a component of the complex can be enzymatically labeled with, for example, horseradish peroxidase, alkaline phosphatase, or luciferase, and the enzymatic label is then detected by determination of conversion of an appropriate substrate to product.

Determining the ability of the test compound to interfere with the Vif self-association can also be accomplished using technology such as real-time Biomolecular Interaction Analysis (BIA) as described in Sjolander et al., 1991, Anal. Chem. 63:2338-2345 and Szabo et al., 1995, Curr. Opin. Struct. Biol. 5:699-705. BIA is a technology for studying biospecific interactions in real time, without labeling any of the interactants (e.g., BIAcore, BIAcore International AB, Uppsala, Sweden). Changes in the optical phenomenon of surface plasmon resonance (SPR) can be used as an indication of real-time reactions between biological molecules.

In more than one embodiment of the methods of the present invention, it may be desirable to immobilize particular Vif dimers to facilitate separation of complexed from uncomplexed forms of one or both of the molecules, as well as to accommodate automation of the assay. The effect of a test compound on the Vif:Vif complex, can be accomplished using any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/target fusion proteins can be adsorbed onto glutathione sepharose beads (Sigma Chemical, St. Louis, Mo.) or glutathione-derivatized micrometer plates, which are then combined with the other corresponding component of the Vif:Vif complex in the presence of the test compound. The mixture is incubated under conditions conducive to complex formation (e.g., at physiological conditions for salt and pH). Following incubation, the beads or microtiter plate wells are washed to remove any unbound material, the matrix is immobilized in the case of beads, and the formation of the complex is determined either directly or indirectly, for example, as described above.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223, 409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical to that new chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery.

In one embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a," "and," and "the" include plural references unless the context clearly dictates otherwise. All technical and scientific terms used herein have the same meaning.

Publications discussed herein are provided solely for their disclosure prior to the filing date of the described application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1

Assay Development for High Throughput Molecular Screening

I. Specific Aims

The proposed research seeks to develop a novel high throughput screen based on quenched FRET to identify small molecules that bind to the HIV protein known as Viral Infectivity Factor (Vif) and disrupt its self-association. The primary function of Vif is to bind to the host-defense factor known as APOBEC3G (A3G) and induce A3G degradation through a polyubiquitination-dependent proteosomal pathway. Although Vif was discovered more than a decade ago, its requirement was only known as 'being essential for infection of non-permissive cells'. The function of Vif was revealed in the discovery of A3G as a host-defense factor. A3G binds to single-stranded replicating HIV DNA and introduces multiple dC to dU mutations in the negative strand that templates dG to dA mutations in the protein-coding strand of HIV in the absence of Vif. During the late phase of HIV infection, A3G can become packaged with virions such that it is in position to interact with nascent DNA during viral replication upon infection. Vif prevents A3G viral packaging while also reducing the cellular abundance of A3G thereby promoting viral infectivity.

Research by our lab and others revealed that multimerization of Vif through a small C-terminal motif, $^{161}$PPLP$^{164}$, was required for the interaction of Vif with A3G. The critical importance of Vif self-association through this motif was demonstrated with Vif multimerization antagonist peptides that also contained the HIV TAT membrane transduction motif in order to penetrate cells. This peptide prevented co-immunoprecipitation of Vif, markedly reduced Vif-dependent A3G destruction and restored A3G antiviral activity in the presence of Vif. Ultimately small molecules with Vif multimerization antagonistic activity are of greater long-term value in the drug industry. Given the antiviral capacity of the peptide in living cells we believe Vif multimerization is an accessible target in vivo with significance equal to the A3G-Vif interaction. In fact, the C-terminal self-association motif is relatively small and does not overlap with any of the other Vif or A3G interaction domains making it perhaps a more attractive target than the relatively large A3G-Vif interaction domain (residues 40-44 and 52-72) in the N-terminus of Vif.

We seek to develop a primary and secondary screen and apply 'hit' validation assays for small molecules that disrupt Vif's ability to multimerize (directly or allosterically) in order to protect A3G antiviral activity from Vif mediated inhibition. Given the increasing preponderance of HIV strains that are resistant to the current antiviral drugs on the market, a therapeutic against a novel target such as Vif multimerization would have a significant impact on the worldwide epidemic of HIV/AIDS.

Specific Aim 1.

Optimize a primary high throughput screen in 384-well format that is based on Vif multimerization and quenched FRET. EGFP-V5-Vif (the fluorescence donor) and Vif-HA-REACh2 (the acceptor and non-fluorescent YFP variant that quenches EGFP fluorescence) will be co-expressed in HEK 293T cells. Compounds that dissociate Vif multimers will induce EGFP fluorescence making this a positive screen for small molecules that disrupt Vif self-association.

Specific Aim 2.

Develop and optimize a secondary screen in microtiter well format to validate 'hits' from the primary screen. In this *E. coli*-based assay, one Vif is linked to the periplasmic transporter signal peptide ssTorA and another Vif is linked to β-lactamase (Bla). In order for cells to survive under ampicillin selection the Vif linked to ssTorA must multimerize with Vif linked to Bla thereby enabling transport of Bla to the periplasm where it neutralizes ampicillin. In the presence of small molecules that disrupt Vif self-association the bacteria will not grow in the presence of ampicillin.

Specific Aim 3.

Perform 'hit' validation assays to confirm that small molecules selected by the primary and secondary screens have antiviral activity through their antagonism of Vif self-association. Antiviral activity will be validated for each compound with a luciferase viral infectivity reporter assay using infected TZM-bl cells in microtiter plate format. Each compound's ability to inhibit Vif-Vif interaction will be evaluated by co-immunoprecipitation. Western blot analysis of whole cell extracts and purified viral particles from cells transfected with viral DNA and A3G will demonstrate the efficacy of compounds in protecting A3G from Vif-dependent degradation, thereby enabling A3G packaging within virions.

II. Background and Significance

The virus contains a 10-kb single-stranded RNA genome that encodes three major classes of gene products that include: (i) structural proteins (Gag, Pol and Env); (ii) essential trans-acting proteins (Tat, Rev); and (iii) "auxiliary" proteins that are not required for efficient virus replication in permissive cells (Vpr, Vif, Vpu, Nef) [reviewed in (1)]. There has been a heightened interest in Vif as an antiviral target because of the discovery that the primary function of Vif is to overcome the action of a cellular antiviral protein known as APOBEC3G or A3G (2). In permissive cells (e.g. 293T, SUPT1 and CEM-SS T cell lines) vif-deleted HIV-1 clones replicate with an efficiency that is essentially identical to that of wild-type virus. However in non-permissive cells (e.g. primary T cells, macrophages, or CEM, H9 and HUT78 T cell lines), vif-deleted HIV-1 clones replicate with 100- to 1000-fold reduced efficiency (3-8). The failure of Vif-deficient HIV-1 mutants to accumulate reverse transcripts and generate integrating provirus in the non-permissive cells is due to the ability of A3G to interact with viral replication complexes and impair their progression as well as A3G mutagenic activity on nascent proviral single-stranded DNA (2,9-11).

Discovery of A3G.

The function of A3G (formerly named CEM15) as an antiviral host factor was discovered in 2002 in experiments designed to identify host cell factors in non-permissive cells that would necessitate the expression of Vif (2). Heterokaryons consisting of non-permissive and permissive cells retained the non-permissive phenotype for Vif-deficient virus, demonstrating expression of a dominant neutralizing factor in non-permissive cells (3,4). Subtractive transcriptome analysis identified a cDNA encoding A3G (2) as a member of the APOBEC family of cytidine deaminases active on single-stranded nucleic acids (12,13). Transfection of permissive cells with A3G cDNA was necessary and sufficient for conversion to the non-permissive phenotype for Vif-deficient HIV-1 infectivity (2).

A3G Antiviral Mechanism.

Multiple labs have characterized a deaminase-dependent antiviral function of A3G and its packaging into HIV virions (9-11). Sequencing of proviral genomes revealed that cells infected with virions containing A3G had dG to dA hypermutations throughout the protein encoding positive strand (9-11), consistent with A3G dC to dU mutation of the negative strand during reverse transcription (11). Furthermore, A3G acts processively 3' to 5' along the minus-strand HIV DNA template (14,15) with mutations occurring in regions where the HIV DNA is single-stranded for the longest period of time during HIV reverse transcription (16,17). The hypermutations introduce multiple premature stop codons and codon sense changes that negatively affect the virus (9-11). The dU mutations in minus-strand viral DNA can trigger the uracil base excision pathway mediated by uracil DNA glycosylase (UDG) that is recruited into virions (18,19), leading to cleavage of viral DNA before integration into host DNA (10). Reduction in proviral DNA can also occur through what has been proposed to be a physical block to reverse transcription by A3G (5,6,20-22).

Vif-Dependent Inhibition of A3G Antiviral Activity.

Vif-expressing viruses overcome A3G by suppressing viral packaging of A3G and targeting it for proteosomal degradation (23-26). Vif promotes A3G degradation through its ability to bind to the ubiquitination machinery. A consensus SOCS (suppressor of cytokine signaling)-box in the C-terminus of Vif (residues 144-SLQYLA-149) binds to the Elongin C subunit of the E3 ubiquitin ligase complex that also contains Cullin 5 and Elongin B (26). Vif also contains a zinc binding HCCH motif (residues 108-HX5-CXBCX5H-138) that confers an interaction with Cullin 5 (27). Vif serves as a bridge for A3G to Elongin C and Cullin 5 in the E3 ubiquitin ligase complex, leading to polyubiquitination of both Vif and A3G (25-27). Recent studies have shown that only polyubiquitination of Vif on one or more of its 16 lysine residues is required for proteosomal degradation of A3G and Vif (28). Site-directed mutagenesis demonstrated that alteration of a single amino acid within A3G could affect Vif interaction (29-31). An aspartic acid at position 128 in A3G is required for HIV-1 Vif to degrade human A3G whereas a lysine at position 128 is required for simian immunodeficiency virus from African green monkey (SIVagm) Vif to degrade agmA3G (29-31). Alanine scanning mutation analysis of A3G revealed that residues adjacent to D128 are also crucial for Vif interaction with A3G, specifically proline 129 and aspartic acid 130 (32). On the other hand, relatively large regions within the N-terminus of Vif are involved in its interaction with A3G. Deletion and point mutation analyses of Vif identified residues 40-YRHHY-44 and 52-72 as being critical regions within Vif responsible for A3G interaction and degradation (33-36).

Vif Self-Association.

An analysis of Vif deletion mutants in the Zhang lab at Thomas Jefferson University in 2001 revealed that residues 151-164 were critical for Vif multimerization, an interaction that was required for infectivity of non-permissive cells (37). Subsequent phage display revealed that peptides with a PXP motif bound to PPLP within Vif (residues 161-164), and in doing so blocked Vif multimerization in vitro (38). Upon linkage of a cell transducing peptide to PPLP containing peptides of Vif, both the Zhang lab (using antennapedia homeodomain, RQIKIWFQNRRMKWKK) and our lab (using HIV TAT transduction domain, YGRKKRRQRRRG) revealed that these peptide chimeras transduced cells and blocked live HIV infectivity (38,39). A3G incorporation into viral particles was enhanced in the presence of the peptide resulting in marked suppression of HIV infectivity (39). Donahue et al. demonstrated that mutating the PPLP motif to AAAP enabled A3G antiviral activity. More importantly, they showed through co-immunoprecipitation analysis that the Vif multimerization mutant had significantly reduced interaction with A3G. On the other hand, the Vif mutant retained interactions with Elongin C and Cullin 5 in a manner equivalent to wild-type Vif (40). The data reveal that Vif self-association is essential for both viral infectivity and Vif interaction with A3G. Moreover, the Vif multimerization domain can be disrupted in vivo, demonstrating its potential as a drug target.

Advantage of Targeting Vif Self-Association.

To date, four characteristics of Vif-A3G interaction have been studied in enough detail to make them of potential interest as drug targets. These are: (i) Vif self-association, (ii) the Vif surface and (iii) the A3G surface that contribute to the interface of Vif-A3G complexes, and (iv) Vif polyubiquitination.

Vif polyubiquitination may be the most difficult functionality of Vif to selectively target, because there are 16 lysines on Vif that are capable of being polyubiquitinated (28).

Small molecules that affect ubiquitination of Vif are likely to be toxic given that ubiquitin-mediated degradation is an essential part of the cell and 'hits' on this target are likely to have off-target effects leading to toxicity. Moreover, Vif bound to A3G that is not degraded would likely still prevent A3G viral packaging.

There has been some promising work involving the Vif-A3G interface. The Gabuzda lab evaluated 15-mer peptides of Vif regions for their ability to antagonize the Vif-A3G interaction. A peptide containing amino acids 57-71 of Vif was identified that blocked Vif-A3G interaction in vitro (41). However the efficacy of this peptide as an antiviral in vivo is yet to be determined. The Rana lab has identified a small molecule that is capable of blocking Vif-dependent degradation of A3G in HEK 293T cells through HTS based on Vif-dependent degradation of a fluorescently tagged A3G. The molecular target of the small molecule and its mechanism of action are unclear (42).

Considering A3G as a drug target, the major caveat to targeting the N-terminal region of A3G involved in Vif binding is the fact that the same region of A3G is also involved in crucial interactions for its cellular and antiviral activity. Deletion analysis revealed that residues 104-156 of A3G were crucial for HIV Gag binding and viral packaging (43,44). Also, scanning alanine mutagenesis demonstrated that amino acids 124-YYFW-127 were especially important for viral packaging (32). The Smith lab recently showed that there is a cytoplasmic retention signal in residues 113-128 of A3G that interacts with an as-of-yet unidentified cytoplasmic partner that prevents A3G from entering the nucleus (45). The related proteins, APOBEC1 and AID, must traffic to the nucleus but their nuclear import and access to genomic DNA are strictly regulated (46) to prevent their potential genotoxicity due to unregulated DNA deaminase activity (47-53). Therefore, small molecules that prevent A3G binding to Vif at residues 128-130 of A3G (32) have the potential negative outcome of affecting A3G viral packaging or enabling A3G access to the genome.

We propose that the Vif multimerization domain is an attractive target for drug development. Blocking the Vif self-association has proven to be an accessible target in vivo and disrupting Vif self-association prevents Vif-A3G interaction in a manner that will prevent the degradation of A3G and preserve its antiviral activity (38,39). Preliminary data will demonstrate the practicality of using Vif for the development of HTS that are biased for Vif multimerization.

Based on these considerations, the goal of this proposal is to develop a human cell-based homogenous assay as a primary HTS and an orthogonal secondary screen in *E. coli* for small molecules that antagonize Vif self-association. Viral infectivity assays, co-immunoprecipitation of differentially tagged Vif subunits and whole cell A3G quantification and A3G viral encapsidation will serve as functional endpoints to validate hits obtained from a preliminary library screening.

III. Preliminary Results

Vif Self-Association is an Accessible Target.

Our studies with a peptide containing the Vif multimerization motif and the HIV TAT transduction motif demonstrated that Vif self-association is accessible in vivo. The peptide prevented live HIV viral infection of H9 and MT-2 T cell lines that endogenously express A3G. After twenty days of infection the peptide blocked viral infectivity, reducing reverse transcriptase (RT) activity in cell supernatants to levels that were on par with those from no virus cell control or cells treated with the potent antiviral AZT. The reduction in infectivity was dependent on the presence of Vif and A3G (39) and the peptide specifically allowed 2.6-fold more A3G to enter viral particles as evident when the A3G western blot signals of (+) and (−) peptide were normalized for p24 gag recovery. This demonstrated that targeting Vif self-association alleviated the Vif-dependent inhibition of A3G viral packaging.

Development of the Quenched FRET Primary Screen.

EGFP is a FRET donor and REACh2 (Resonance Energy Accepting Chromoprotein 2) is a non-fluorescent FRET acceptor (54). The non-fluorescent REACh2 is able to quench EGFP signal in a distance-dependent manner when they are linked to interacting domains. However, if there is no interaction, EGFP and REACh2 are not proximal and quenching will not occur. This is an ideal system for HTS in which the default condition is quenched signal due to interacting Vif molecules linked to the FRET pair. A small molecule 'hit' will produce a positive fluorescent signal by interfering with Vif self-association and alleviating the quench.

We tested various combinations of N- and C-terminally tagged Vif constructs and determined that EGFP-V5-Vif and Vif-HA-REACh2 yielded the most significant quench. The system employs the use of HEK 293T cells due to their high transfection efficiency (up to 90% with FUGENE 6 or HD® lipofection reagent) and Vif's established functionality in these cells demonstrated by many investigators (24,29,32, 42). Transient transfection allows for high expression of the protein, which is important for robust FRET signals. In addition, transiently transfected cells have the ability to maintain an expression level of REACh2-HA-Vif that is higher than EGFP-V5-Vif to ensure maximum amount of quenched protein in the cell. In fact stable cell lines expressing the FRET pair have been established but these proved to have lower levels of Vif expression than transiently transfected cells and consequently produced very low signals.

DNA ratios greater than or equal to 4:1 REACh2 to EGFP maintained quenched signal in the vast majority of cells. EGFP-V5-Vif alone has a strong baseline fluorescence. When EGFP-V5-Vif and Vif-HA-REACh2 are co-expressed there is a significant reduction in fluorescence intensity due to REACh2 quenching of EGFP signal. Addition of the Vif multimerization antagonist peptide (described above) at 50 µM liberates EGFP-V5-Vif and relieves the quench. Cells treated with the peptide antagonist will serve as a positive control condition in the assay.

There was no quench with the multimerization-deficient 4A-Vif mutant (161-PPLP-164 to AAAA) in the equivalent conditions to wild-type Vif. As expected the addition of peptide to cells expressing mutant 4A-Vif did not promote additional fluorescence. Westerns for HA and V5 demonstrated consistent expression of the transfected constructs confirming that the lack of fluorescence is not due to less expression of the EGFP-V5-Vif, but is in fact due to quenched FRET.

Adapting the Quenched FRET Assay to 96-Well and 384-Well Format

Experimentals relating to adapting the quenched FRET assay to 96-well and 384-well format are set forth below:
Description of reagents and readouts: We are currently capable of screening small libraries in 96-well format, and have optimized transfections for 384-well format. The assay is cell based transient transfection of two plasmids. One plasmid contains EGFP-V5-Vif (EVV)

and the other contains Vif-HA-REACh2 (VHR). REACh2 is a non-fluorescent YFP variant that quenches EGFP through FRET, so in the default state Vif dimerizes and the EGFP signal is quenched, a compound that affects the interaction will cause an increase in fluorescence due to lack of FRET from interacting proteins (aka "releasing of the quench"). Our read out is fluorescence at GFP's excitation and emission in a PE Victor 3 plate reader. We have to express the REACh2 protein 4 times higher than the EGFP in order to ensure good quench and we could not recapitulate that in stable cell lines at the consistency, ratio and expression level we can achieve with transient transfection.

Data confirming assay protocol: We have gone through a significant amount of troubleshooting to obtain Z'-factors and CVs that are optimal for HTS. We have also worked out a background correction to account for variability within plates and between plates. Using this optimized protocol the Z'-factors are always above 0.5 in our hands. We have a peptide that we have tested as a positive control that registers as a dose dependent "hit" with a Z-score <3. We also have some promising small molecules from the NCC library that passed secondary validation by counterscreening for toxicity and antiviral activity.

Signal of sufficient intensity: Using the GFP/FITC excitation and emission of 485 and 535, respectively, in the PE Victor 3 Multilabel Plate Reader quenched signal is typically >20,000 RFU above background and the positive control is >100,000 RFU above the quenched condition. These values can vary depending on exposure time for the plate read and aperture size, but this is a typical signal range for a one second reads using a normal aperture size setting.

CVs and Z'-factors:
  96-well format numbers from pilot screen:
    CV quench=2.4%
    CV positive control=3.6%
    Z'-factor=0.51
  384-well format numbers:
    CV quench=1.4%
    CV positive control=3.3%
    Z'-factor=0.66

Figure 6:
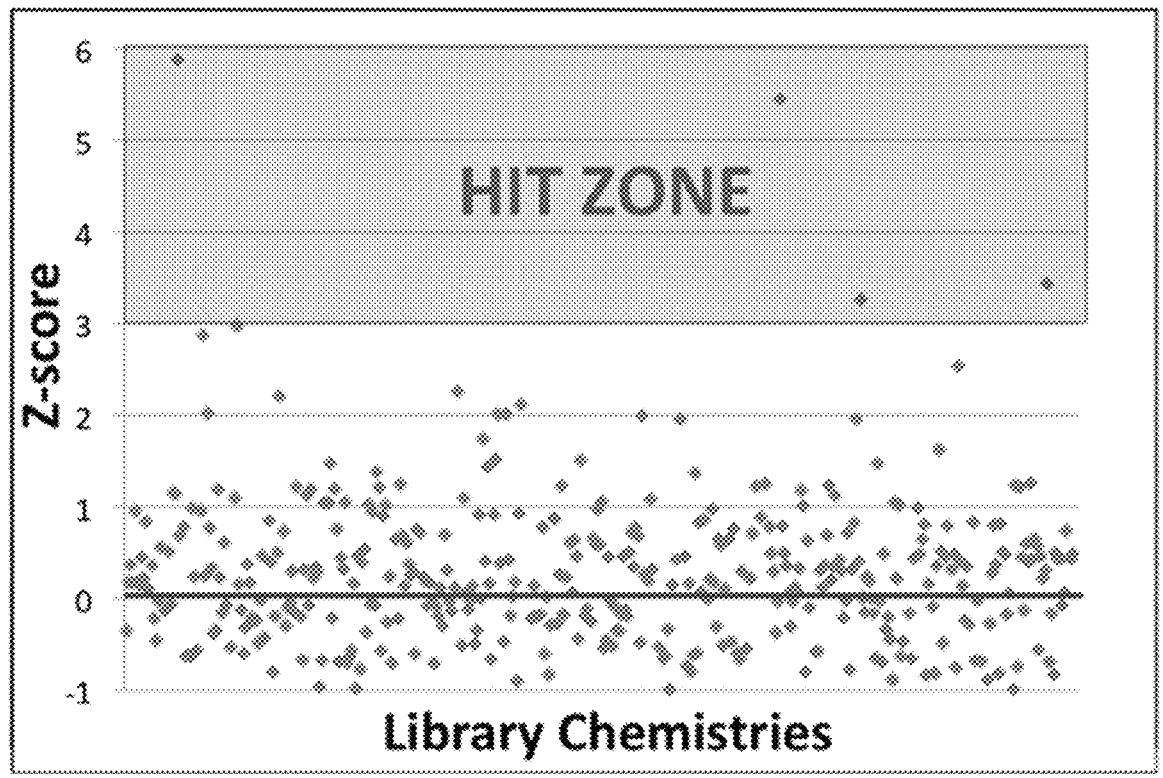
FIG. 6 is a graph showing hit rate from screening a small library of compounds using one embodiment of an assay according to the present invention.

Oya001 peptide "hit" control.
  Standard Deviation of 980=1 Z-score
  This experiment involved three test wells for each concentration of Oya001 peptide and 15 controls for quenched and positive signal. Plate reads were performed before adding peptide and 1.5 hours after peptide addition. The differentials between these two reads were used in the analysis (ARFU).
    CV quench=1.7%
    CV positive control=1.9%
    Z'-factor=0.63
  We have published data showing that this peptide directly affects our target (39). The data in FIG. 6 shows a clear dose dependence with the peptide in the HTS assay revealing z-scores of 1.36, 1.96, 3.01, and 4.37 that relate to the $91.2^{th}$, $97.4^{th}$, $99.9^{th}$ and $>99.9^{th}$ percentile for 12.5, 25, 50, and 75 τM of Oya001 peptide, respectively.

Knowledge of control parameters
  DMSO tolerance
    The assay tolerates DMSO very well at 0.1-1%, See the toxicity test reported in FIGS. 11A-11B, in which the SMVDAs or DMSO alone were added at 1%. Moreover, all pilot screens were performed at ~0.1% DMSO and SMVDAs or DMSO alone (controls) were added to cells anywhere between 0.1-0.5% in the HIV infectivity counterscreens.

Plate-to-Plate variation (384-well plates with 40±samples per plate)
  Plate 1:
    CV quench=1.4%
    CV positive control=5.2%
    Z'-factor=0.63
  Plate 2:
    CV quench=1.6%
    CV positive control=4.7%
    Z'-factor=0.66
  Plate 3:
    CV quench=2.0%
    CV positive control=5.9%
    Z'-factor=0.59
  CVs for Average RFU values from Plates 1-3
    CV quench=0.9
    CV positive control=2.5%

Background Correction
  Z-Score Normalization allows for cross plate comparison of experimental data points by making all plate means and standard deviations equal via the plate variability correction procedures shown in equation 1 and 4. Further calculating the systematic variability (equation 2) and applying the correction (equation 3) controls for variability due to error in plating, cell growth or other systematic error. Finally, Z-Score transformation allows data to be fit against a normal distribution. This takes the arbitrary nature of 'Relative Fluorescent Units' and frames the data in the context of a Z-Score, or deviation. HTS hits are generally selected as a function of deviation from the sample population, thus framing the data in an easily interpreted context through this normalization procedure.

Equations:
Initial Plate Normalization $$x'_i = \frac{x_i - \mu}{\sigma} \quad (1)$$

Normalizes data $(x_j)$ so plate mean ($\mu$) and plate standard deviation ($\sigma$) are 0 and 1, respectively.

Well Background Calculation $$z_i = \frac{1}{N} \sum_{j=1}^{N} x'_{i,j} \quad (2)$$

Calculates systematic background of $z_i$ from the mean of data points x' of well i across plates j of plate set 1, 2, ..., N. All data points x'≥3 are excluded when N≤100.

Well Background Correction $$x''_i = x'_i - z_i \quad (3)$$

Subtracts systematic background $z_i$ from normalized data point x' yielding background corrected data point x"

Re-Normalization Post-Background Correction $$x_i''' = \frac{x_i'' - \mu}{\sigma} \tag{4}$$

A final re-normalization using corrected data x", subtracting plate mean, µ, and dividing by plate standard deviation, σ. This corrects plate µ and σ back to 0 and 1 for cross plate comparison.

Development of an Orthogonal E. coli Based Secondary Screen.

The secondary screen takes advantage of the Twin-arginine translocation (Tat) pathway found in plants and bacteria (55). The Tat pore is in the cytoplasmic membrane of E. coli and is made up of three proteins, Tat A, B and C. A small N-terminal signaling domain (i.e. ssTorA) is recognized and cleaved in transport. Folded proteins and protein complexes of two or more intact proteins, where only one protein carries a Tat signal, can be exported by the Tat pathway in a process termed the "hitchhiker" mechanism (55,56). β-lactamase must be transported to the periplasm to breakdown ampicillin (Amp), thus mediating growth under Amp selection. This assay has been successfully adapted to study protein-protein interactions and used as a screen for compounds that affect these interactions (57,58).

OyaGen, Inc has obtained a license to use this system from Vybion, Inc (www.vybion.com/?page=techprocode). We have re-engineered the assay to co-express ssTorA-Vif and β-lactamase (Bla)-Vif under L-arabinose (Ara) induction in E. coli. Multimerization of Vif links ssTorA-Vif to Bla-Vif, allowing Tat-mediated transport of Bla-Vif to the periplasm. In the presence of small molecules that prevent Vif multimerization, Bla-Vif cannot be transported to the periplasm and cells will not survive.

The constructs pBAD18-Cm-ssTorA-V5-Vif and pBAD33-Kan-Bla-HA-Vif have been cloned, and found to express well in the MC4100 E. coli strain as confirmed by western blotting. pBAD18 is a high copy plasmid whereas pBAD33 is a low copy plasmid. Bla-Vif was put in the low copy plasmid to avoid Amp resistance due to an overabundance of Bla-Vif in the media that can leach out of dead or dying cells. Initial tests in 96-well format carried out as five 200 µl cultures revealed no differential growth +/−Ara in the absence of Amp. When Amp was added (30 µg/mL) to cultures simultaneous with Ara, antibiotic resistant growth became apparent by 2 hours following Ara induction. The difference in growth between cultures +/−Amp continued to increase up to the termination of the study at 8 hours. Data in FIG. 9 are the average of three repeats of the experiment. At 8 hours, the difference was 0.419 average OD 600 readings +/−Ara induction. The standard deviations were low at 0.021 for +Ara and 0.005 for −Ara, suggesting a possible Z'-factor favorable for HTS at 0.807.

We will further evaluate media conditions that effect bacterial growth rate (10, 50 LB, supplemented with minimal media (M9) salts and 'super' broths) in an effort to improve the differential between +/−Amp. This is important to achieve good differential growth as early as possible and obtain the best coefficient of variance, signal to noise ratio and Z'-factor. Dependence of this HTS secondary screen on the Vif multimerization domain and DMSO tolerance also will be determined.

Example 2

Screening, Validating, and Vetting Vif Dimerization Disruptors

Part 1. Validating the Assay.

HTS analysis of Vif-Vif multimerization through quenched FRET utilizes Vif-HA-REACh2 (quencher) and EGFP-V5-Vif (fluorophore) at an optimized ratio of plasmids transiently transfected into 293T cells. The interaction of Vif molecules enables quenching of EGFP signal by REACh2. Control experiments with either peptides that mimic this domain prevented Vif-Vif interaction or mutations within the PPLP domain crucial for Vif-Vif interaction prevent quenching and have stronger fluorescence signals. The legend describes the abbreviations used. Western blotting of extracts from transfected cells showed equivalent expression of the donor/quencher pair mutant constructs and donor/quencher pair in peptide treated cells when compared to control.

Part 2. Screening a Small Library.

The screen has been optimized to yield CVs less than 3% and a Z' factor of 0.61 in 96-well format. To date two libraries have been screened totaling 2446 compounds at 5 µM, with a smaller subset tested by qHTS at 50, 25, and 5 µM concentrations. In these libraries eight small molecules had to be ruled out due to auto-fluorescence. After background correction and normalizing of values for plate position variability in the screen, 26 small molecules were determined to be hits (SMVDA1-26 for Small Molecules Vif Dimerization Antagonists 1-26). The hit rate was ~1%.

Hits were selected based on three criteria: 1) High hit (Z-score ≥1.8, ~97% and above the normal distribution), 2) Multiple hits (two or more Z-score values ≥0.9, ~82% and above the normal distribution in the three concentrations tested), and 3) Dose dependence. All small molecules with at least one of these criteria were assessed and 24 of the top 26 had at least two of the three criteria. Two exceptions were SMVDA2 and SMVDA17 which only met one criteria (SMVDA2 was a high hit at the lowest concentration tested and SMVDA17 had a Z score of 1.4 for both of the lowest concentrations tested (so relatively close to the high hit cut off of 1.8).

Part 3. Vetting the Hits for Toxicity.

We next analyzed hits for toxicity. We focused on hits that showed dose dependence or were 'high hits' at multiple concentrations. We analyzed toxicity of the compounds at 50, 25, and 5 µM using Promega's Cell-titer Glo, a luciferase based assay that determines ATP concentration. 10,000 cell/well of 293T cells were plated into 96-well format and dosed in triplicate with the small molecules and analyzed with the Cell-titer Glo kit 24 hours later. The data showed that SMVDA1-14 had low to no toxicity at all doses, while SMVDA15-17 were toxic at 50 and 25 µM.

Some hits were not evaluated for toxicity because they were inconsistent hits in the HTS assay and these included: SMVDA20-22 which were 'high hits' in the HTS assay at 50 µM but showed no dose dependence; SMVDA23-25 which were 'medium hits' at 50 µM, high at 25 µM and low at 5 µM and SMVDA26 which was a 'high hit' at 50 and 5 µM but low at 25 µM.

Part 4. Vetting the Hits for Antiviral Activity.

The antiviral activity of the hits in a single round infection with psuedotyped HIV was assessed. The assay is conducted using producer cells that do or do not express A3G and viruses that do or do not express Vif. The wildtype HIV proviral vector codes for all HIV genes except nef (replaced with EGFP) and env. The delta Vif proviral vector is identical to wildtype except that it contains a stop codon early within the vif gene. Delta Vif+A3G is a strong positive control for this assay because without Vif present, A3G is able to be encapsidated into viral particles and have a strong antiviral effect. Alternatively, in the absence of A3G, both wild type and Delta Vif viruses should have good infectivity.

Virus was made by transfecting these vectors with VSV-G coat protein from a separate vector, as well as V5-APOBEC3G (A3G) in the +A3G conditions. Transfecting the coat protein on a separate vector, allows for only a single round of infection. The ratio of proviral DNA:VSV-G:A3G was set to 1:0.5:0.05, which established levels of A3G that were comparable to endogenous A3G. Cells were dosed with chemistries 5 hours after transfection and viral particles were harvested from the media 24 hours after transfecting by filtering through a 0.45-micron syringe filter. Viral load was normalized with a p24 ELISA Kit (Zeptometrix, Buffalo, N.Y.). Equal viral loads were then added in triplicate to TZM-bl reporter cells that express luciferase from the HIV-LTR promoter. 48 hours after infection luciferase levels were assessed with Steady-Glo reagent (Promega).

The first chemistries tested showed dose dependence and were high hits at high compound concentrations in HTS. SMVDA1, SMVDA11-15, and SMVDA18-19 were tested at 50 and 25 µM with A3G present in the first infectivity assay. The criteria for a compound as having antiviral activity were based on % infectivity relative to DMSO only control. Hits that inhibited infectivity to less than 60% of control were considered to have antiviral activity. Only SMVDA1, 18, and 19 were able to show a significant decrease in infectivity at both concentrations, but SMVDA18 and 19 have not been evaluated further because, although they were not toxic, they also were not positive hits at 5 µM in the HTS assay.

Chemistries that had antiviral activity at lower doses and SMVDA1 were tested in the infectivity assay at 5 µM. Although levels of infectivity were not affected as much as they were for the higher doses tested SMVDA1-6 were able to decrease infectivity to less than 60% of control. SMVDA7-10 had minimal effects on infectivity at 5 µM and were eliminated from further consideration.

Since SMVDA1 seemed to be the best candidate so far, we looked closer at the structure and noticed that a related chemistry was also in the initial screen but had been filtered out because it had a strong auto-fluorescence signal (named SMVDA1.1). Given its close relationship to SMVDA1 we tested SMVDA1.1 further in the infectivity assay side-by-side with SMVDA1 at 5, 1 and 0.5 µM. While SMVDA1 had a strong effect at 50 and 25 µM its antiviral activity at lower doses was not as strong, being somewhat effective at 5 and 1 µM by knocking down infectivity by ~50%, yet having minimal effect on infectivity at 0.5 µM. On the other hand, SMVDA1.1 was able to reduce infectivity to less than 30% of control at all three concentrations tested.

At this stage we had 7 compounds with antiviral activity based on +A3G infectivity assays. All seven hits were tested further for their ability to show a differential in infectivity between +Vif & A3G and −Vif & A3G. The rationale here is that these compounds should show a Vif-selective response if they are truly acting as antagonist of Vif dimerization and sparing A3G. Along these lines, SMVDA4-6 did not have any significant differential between +/−Vif & A3G, thus they were eliminated from further consideration. This left SMVDA1, 1.1, 2 and 3, which all showed some differential between the two conditions. This suggested a certain level of target specificity. The most significant differentials were at 5 µM for SMVDA1 and 0.5 µM for SMVDA1.1.

Part 5. Vetting the Hits for A3G Viral Particle Content.

Another way to observe target specificity is by looking at the amount of A3G that is encapsulated into the viral particle. Since Vif blocks A3G from getting into the virus, more A3G should be present in viral particles isolated from cells dosed with a small molecule that disables Vif's function. This was observed in the case of SMVDA1 and 1.1 and, as seen with the infectivity data, SMVDA1.1 worked better at lower doses and seemed to have the most A3G in the virus at 5 µM. Although it must be noted that more volume was required to normalize the p24 load with 11 and 5 µM SMVDA1.1 compared to other small molecules suggesting that higher doses might be cytotoxic, resulting in lower yield of virus. The fact that even the lowest dose of SMVDA1.1 was effective suggested a true effect on the Vif. Supporting this conclusion was the finding that very little A3G was present in viral particles dosed with SMVDA2 and 3 over a larger range of doses. This suggests that their antiviral activity was not selective for Vif.

Our complete analysis of the hits from the initial screen left us with two related compounds (SMVDA1 and 1.1) that passed all our tests. Given the close relationship between these compounds our selection of these compounds suggest that one chemotype or chemical scaffold has been identified that SAR may optimize for nanomolar target selectivity and lower cell toxicity. Moreover the low micromolar efficacy of these compounds suggests that medicinal chemistry, may be able to identify compounds with nanomolar antiviral IC50 and IC95.

Example 3

Studies and Assays Relating to Small Molecule Vif Inhibitors of the Present Disclosure This example relates to various studies and assays with respect to the identification, testing, and modification of small molecule Vif inhibitors of the present disclosure.

Figure 5A:
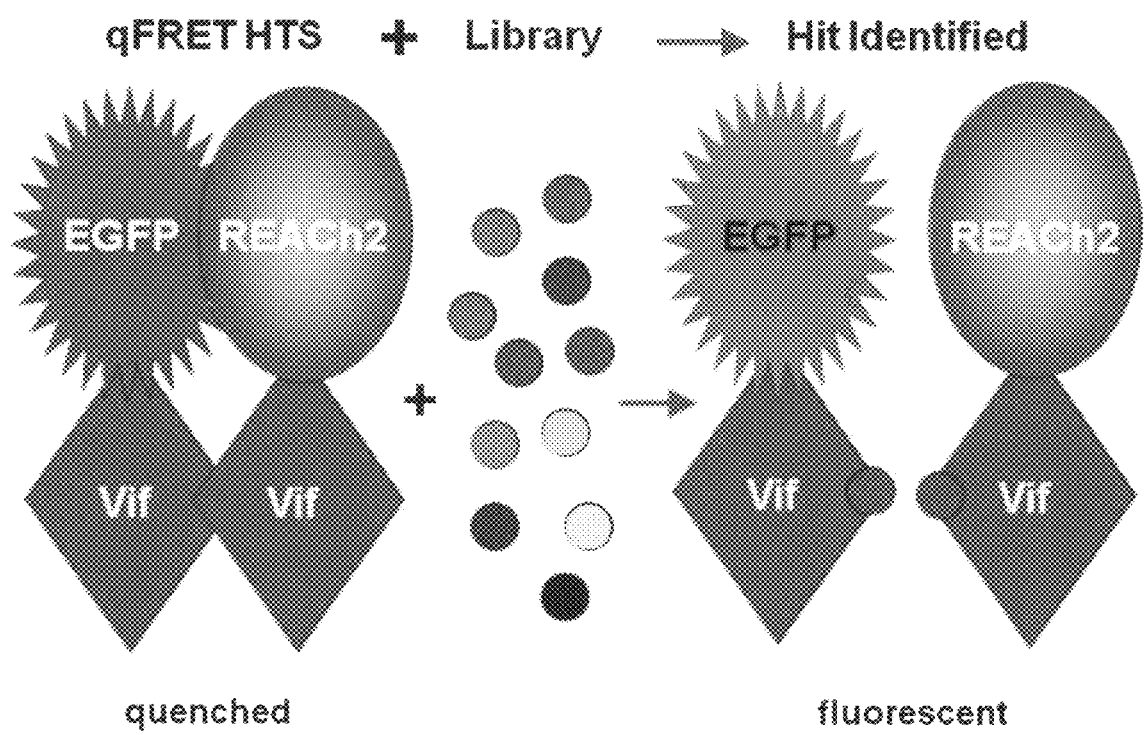
FIG. 5A is a schematic showing the qFRET assay for use in identifying small molecules that interfere with Vif self-association.

As shown in FIG. 5A, a qFRET assay for use in identifying small molecules that interfere with Vif self-association.

As shown in FIG. 5B, an in-cell high throughput screen for Vif dimerization antagonists was conducted. HTS analysis of Vif-Vif multimerization through quenched FRET utilizes transiently transfected Vif-HA-REACh2 (quencher) and EGFP-V5-Vif (fluorophore) at an optimized ratio in 293T cells. The interaction of Vif molecules enables quenching of EGFP signal by REACh2. Control experiments with either mutations within the PPLP domain crucial for Vif-Vif interaction (4A mutant) or peptides that mimic this domain prevented Vif-Vif interaction and consequently resulted in a stronger fluorescence signal (a hit produces a positive signal). The positive control peptide confirmed that Vif-Vif multimerization was responsible for the quenched FRET along with western blotting showing equivalent expression of mutants or peptide treated cells when compared to control. These confirmations established that the assay was optimized for HTS. The screen has been optimized to yield CVs less than 3% and a Z' factor greater than 0.6 in 96-well and 384-well formats. Transient transfection is necessary for EGFP-Vif since over expression of Vif inhibits the cell-cycle and stable cell lines are difficult to establish.

As shown in FIG. 6, hit rate from screening a small library of compounds was determined and a hit zone was identified. In this study, a sampling of 446 out of 2446 chemistries was tested.

Figure 7:
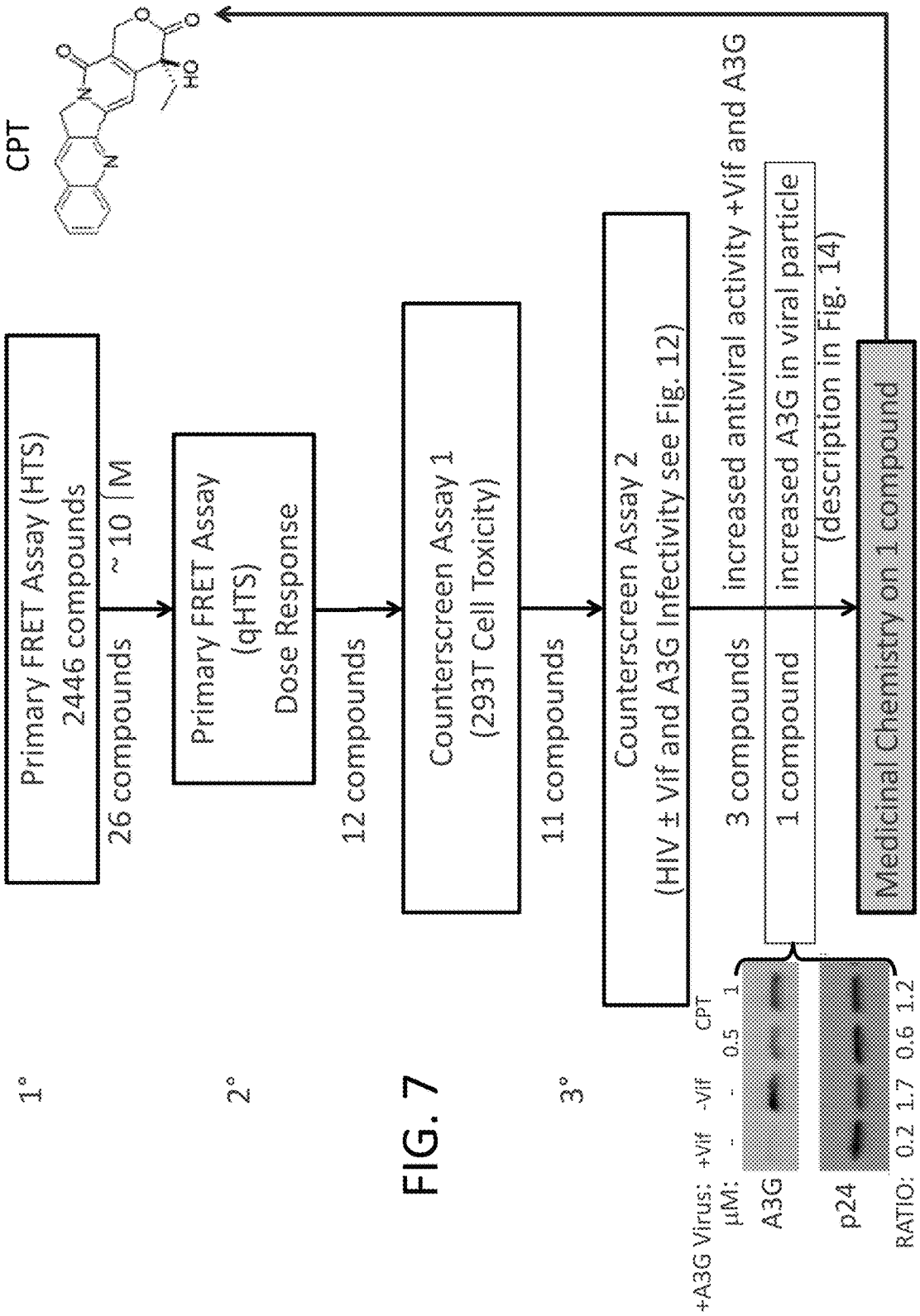
FIG. 7 is a flowchart illustrating one embodiment of a critical path to finding an initial hit for a Vif inhibitor small molecule (e.g., camptothecin, CPT).
Figure 8:
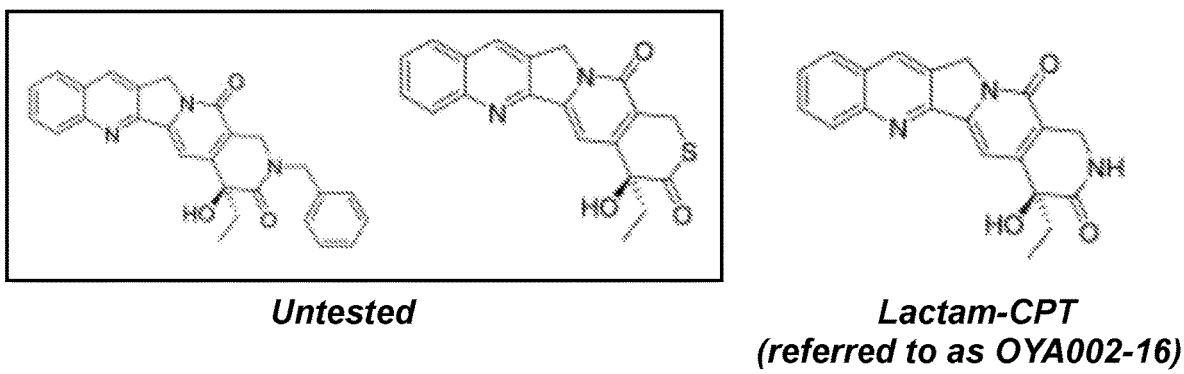
FIG. 8 illustrates aspects of a medicinal chemistry strategy for modifying an initial hit from a Vif inhibitor assay of the present invention for pharmaceutical use.

As shown in FIG. 7, one embodiment of a path to finding an initial hit for a Vif inhibitor small molecule (e.g., camptothecin, CPT) was developed. As shown in FIG. 8, after identifying an initial hit, a medicinal chemistry strategy for modifying the initial hit from a Vif inhibitor assay of the present invention for pharmaceutical use was conducted. For example, one hit related to camptothecin. Camptothecin (CPT) is a known inhibitor of Topoisomerase I (Topo1), which causes toxicity to actively replicating cells. Therefore a CPT derivative that is known to not inhibit Topo1 activity was determined to be a good way to test if CPT derivatives with Vif inhibiting activity could be uncoupled from Topo1 inhibition and toxicity.

Figure 9A:
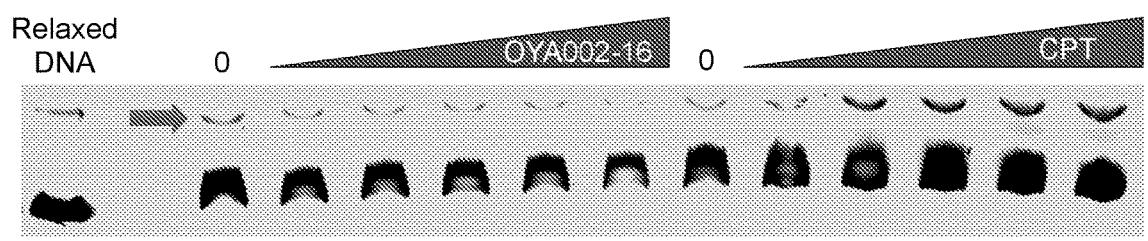
FIGS. 9A and 9B illustrate results of an in vitro drug screening assay for toxicity of the OYA002-16 small molecule of the present invention.
Figure 9B:
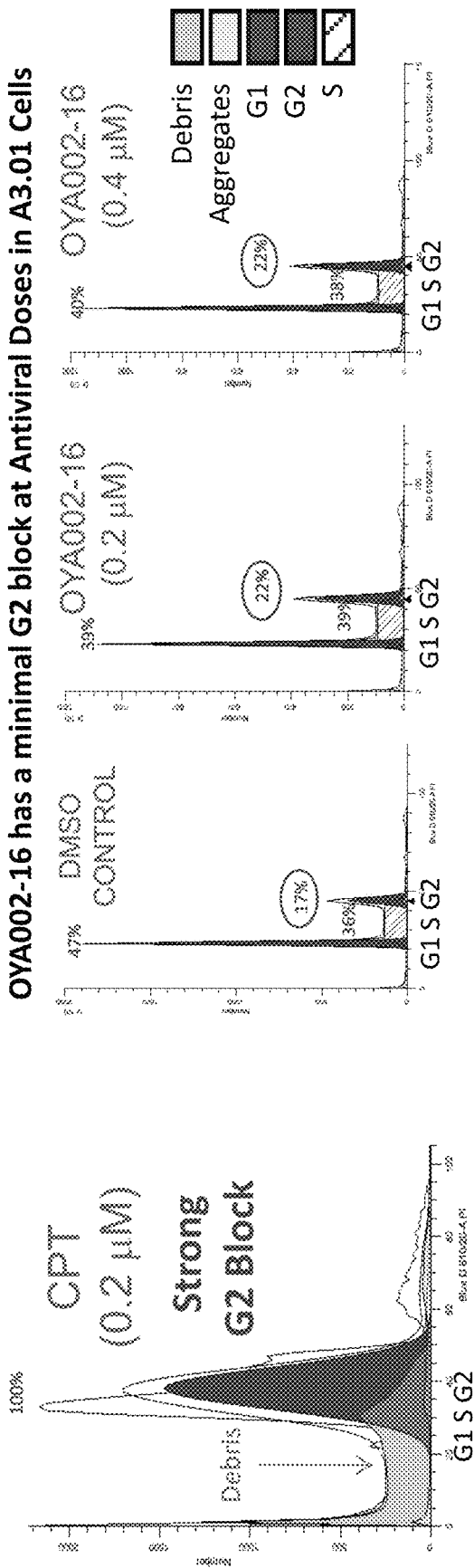

FIGS. 9A and 9B illustrate results of an in vitro drug screening assay for toxicity of the OYA002-16 small molecule of the present invention. As shown in FIG. 9A, in vitro Topo1 drug screening assay (Topogen) shows that increasing amounts of CPT trap plasmid DNA into open nicked circles (increase in top band) while OYA002-16 shows no increase in open nicked circles through Topo1 poisoning compared to the 0 chem control (blue arrow). As shown in FIG. 9B, another test of a compound's effect on toxicity and Topo1 activity is a cell cycle test. After 24 hours of compound treatment cells were fixed in methanol and treated with propidium iodide (PI) to stain the cellular DNA in A3.01 cells (a CEM derived T-cell line). Flow cytometry of the cells can detect if the cells are in the G1 S or G2 phase of mitosis based on amount of PI staining in each cell. Topo1 inhibition causes a strong G2 block as seen with 0.2 µM CPT but 0.2 and 0.4 µM of OYA002-16 had a minimal amount of G2 block (22% in G2 compared to the DMSO control at 17%).

Figure 10:
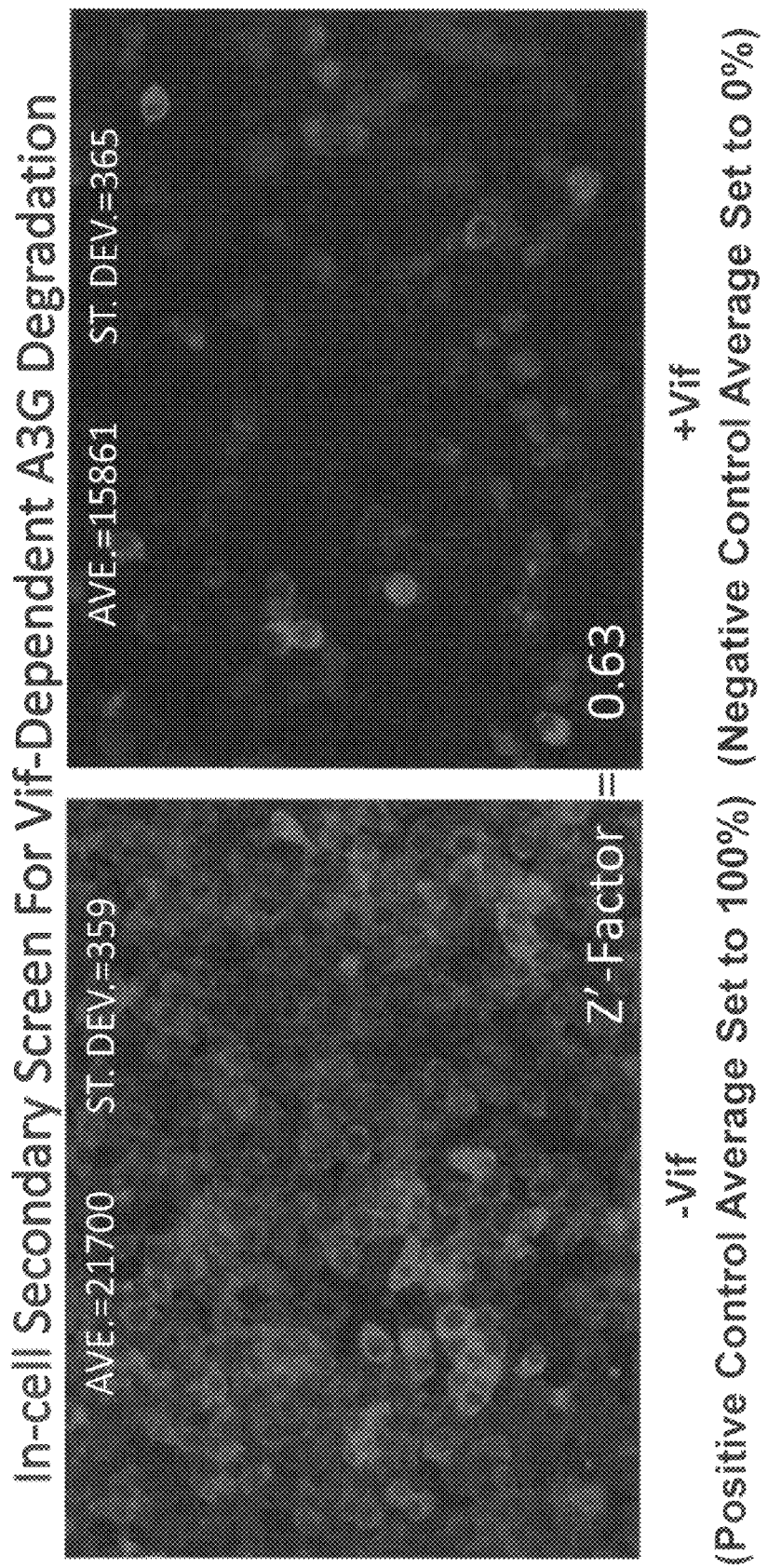
FIG. 10 illustrates in-cell secondary screen fro Vif-dependent A3G degradation.

FIG. 10 illustrates in-cell secondary screen fro Vif-dependent A3G degradation. As shown in FIG. 10, A3G-mCherry is stably expressed in 293T cells under puromycin selection. 50 ng of Vif was transiently transfected into the cells in 384-well format with Turbofect. 4 hours after transfection the chemistries were added to cells. 24 hours after chemistries were added the mCherry signal was read on a Biotek Synergy 4 plate reader. The signal from plated cells not transfected with Vif was averaged and set at 100% (left image), and cells transfected with Vif and treated with DMSO only were averaged and set at 0% (right image). A chemistry that inhibits Vif's ability to chaperone A3G to the proteasomal degradation pathway would result in an increased mCherry signal compared to the DMSO only control, and any signal that is much higher than the no-Vif positive control is likely to be due to autofluorescence from the chemistry itself.

FIG. 11 shows results from a primary screen (left side) and a secondary screen (right side) of the OYA002-16 small molecule scaffold. As shown in FIG. 11, OYA002-16 shows dose dependence in both the primary screen described in FIG. 5A and the secondary screen described in FIG. 10. The primary screen is represented as a change in RFU over the quenched control (ARFU). The secondary screen is compared to the +Vif (0%) and -Vif (100%) controls as described in FIG. 10.

Figure 12A:
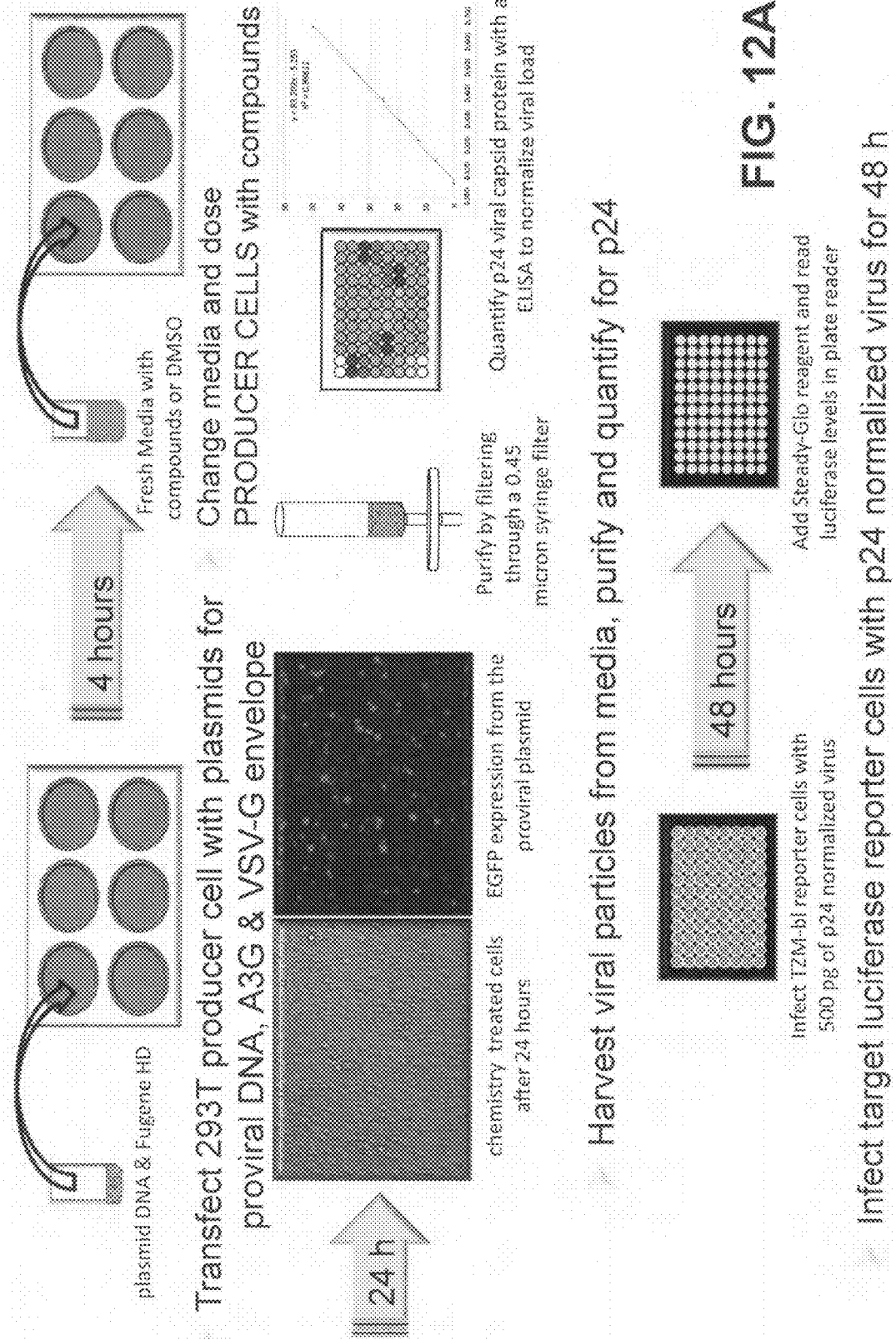
FIG. 12A is a schematic showing aspects of a single cycle infectivity assay of the present disclosure.
Figure 12B:
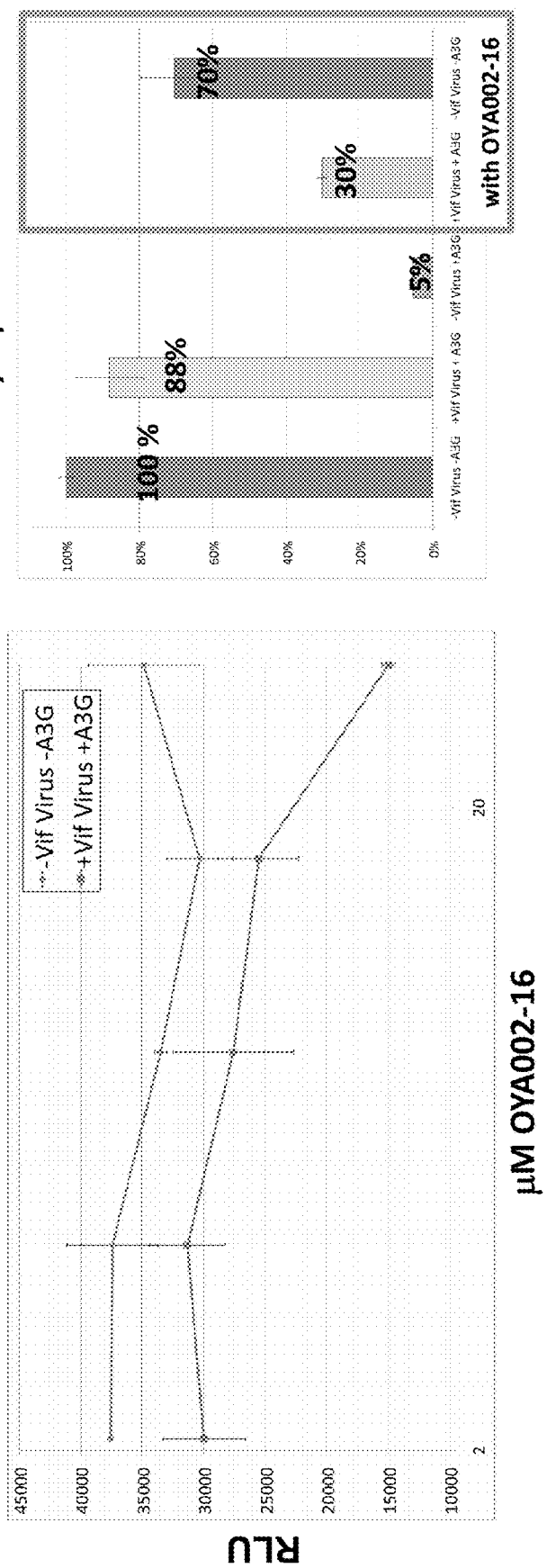
FIG. 12B are graphs illustrating that OYA002-16 maintains an A3G and Vif-dependent antiviral effect in single cycle HIV infectivity experiments. The left graph illustrates pseudotyped single cycle HIV infections. The right graph shows Vif and A3G-dependent effect on pseudotyped HIV infectivity expressed as % of control.
Figure 13:
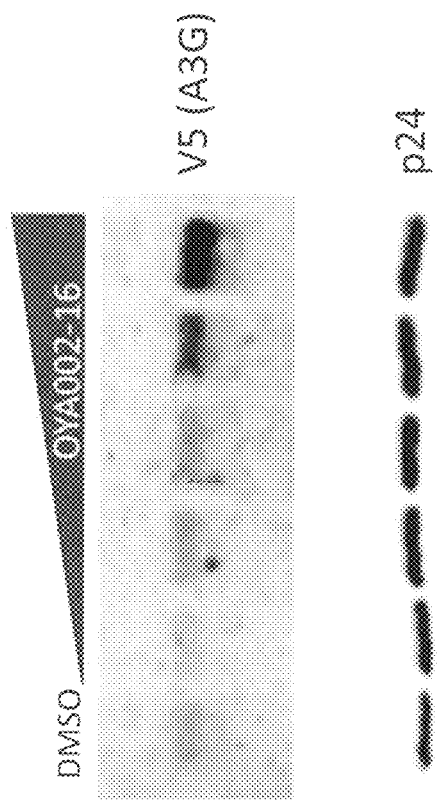
FIG. 13 illustrates results of experiments showing that OYA002-16 increases A3G in viral particles.

As shown in FIGS. 12A and 12B, a single cycle infectivity assay was used to study OYA002-16. FIG. 12A is a visual representation of how the single cycle infectivity experiments were done. They are in 6-well format in order to obtain enough virus to do viral particle purifications for western blot detection of A3G in the viral particle (FIG. 13). The antiviral activity of the hits in a single-round infection with pseudotyped HIV were conducted using HEK293T producer cells +/−A3G and viruses that are +/−Vif. The wild type HIV proviral vector codes for all HIV genes except nef (replaced with EGFP) and env. The DVif proviral vector is identical to wild type except that it contains a stop codon early within the Vif gene. DVif+A3G is a strong positive control for this assay because without Vif present, A3G is able to be encapsidated within viral particles and have strong antiviral activity. Alternatively, in the absence of A3G, both wild type and DVif viruses should have high infectivity.

Single-round infectivity assays utilized transient co-transfection of the viral vectors with VSV-G coat protein vector and V5-A3G in the +A3G conditions using Fugene HD (Promega). Proviral DNA:VSV-G:A3G were added to cells with a ratio of 1:0.5:0.08 which establishes levels of A3G that are comparable to endogenous A3G. These virus producer cells were dosed with compounds four hours after transfection and viral particles were harvested from the media 24 hours after transfecting by filtering through a 0.45-micron syringe filter. Viral load was then normalized with a p24 ELISA (Perkin Elmer).

The infections utilized TZM-bl reporter cells that contain stably integrated luciferase that is driven by the HIV-LTR promoter, therefore luciferase is expressed upon successful HIV infection. Triplicate infections in 96-well plates at 10,000 cells/well with 500 pg p24/well proceeded for 48 hours before the addition of SteadyGlo™ Reagent (Promega) to each well for 30 minutes. Luminescence was measured as a quantitative metric for changes in infectivity with each compound as compared to controls, in which relative luminescence units (RLU) with no compounds are set to 100%.

The gold standard for a Vif dimerization antagonist is antiviral activity that is Vif- and A3G-dependent. This is best represented as a differential between infectivity in the presence of Vif and A3G vs the absence of Vif and A3G.

As shown in FIG. 12B, OYA002-16 showed a dose dependent antiviral effect only when Vif and A3G were expressed (left). The highest concentration of 33.3 µM is shown as a % of controls in the absence of OYA002-16 (right).

FIG. 13 illustrates results of experiments showing that OYA002-16 increases A3G in viral particles. As shown in FIG. 13, +Vif virus+A3G produced in 293T cells in the presence of increasing amounts of OYA002-16 (1.67 µM to 33.3 µM) were purified through a 20% sucrose cushion and western blotted for p24 and V5 tagged A3G (same virus was used in infectivity experiments in FIGS. 12A and 12B).

Figure 14:
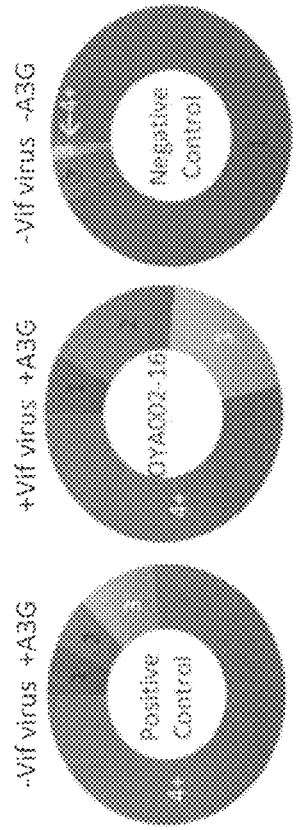
FIG. 14 is an illustration relating to a Next Gen Sequencing for A3G signature mutation profiles.
Figures 1, 16A:
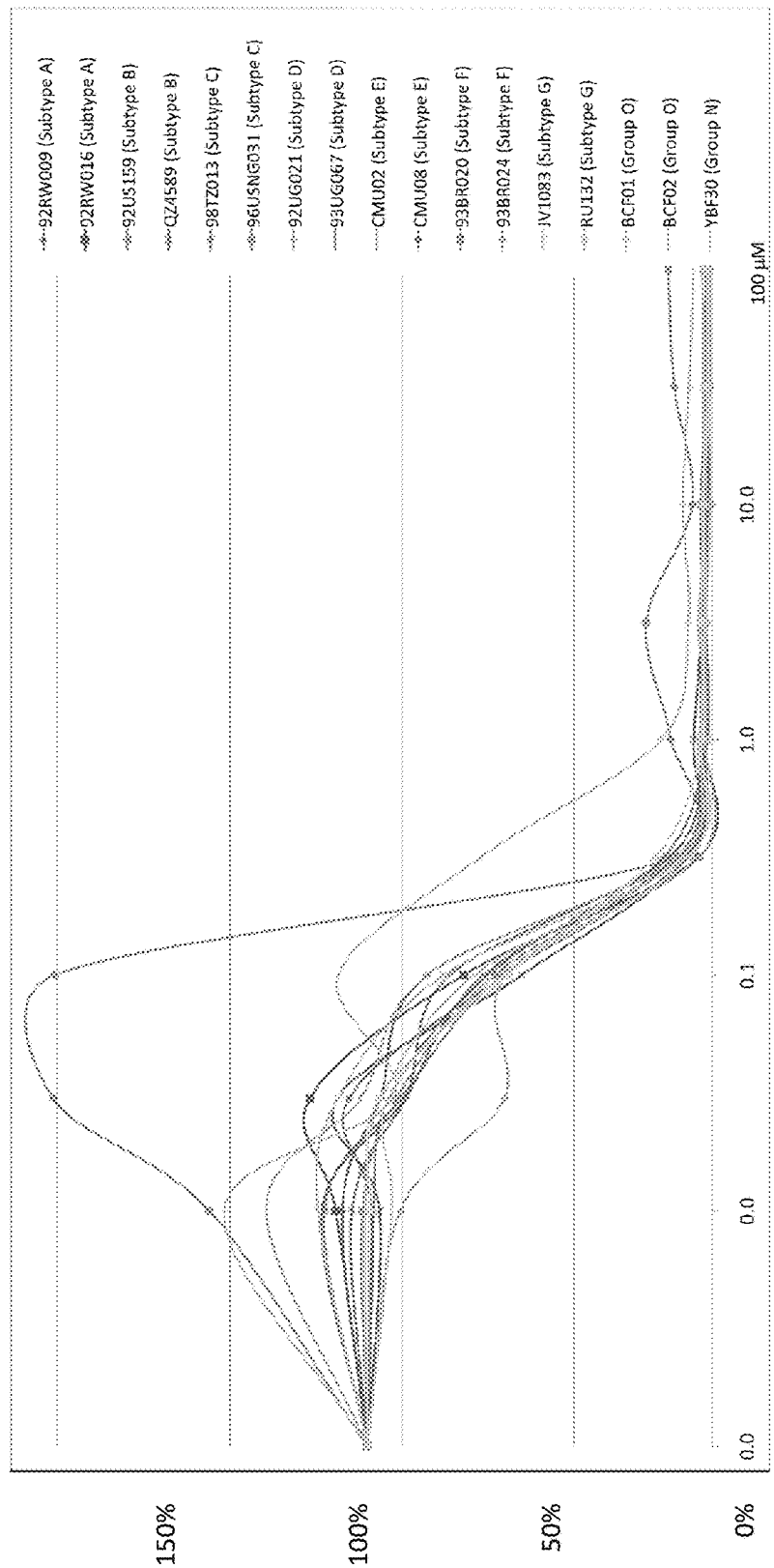
Figures 2, 16A:
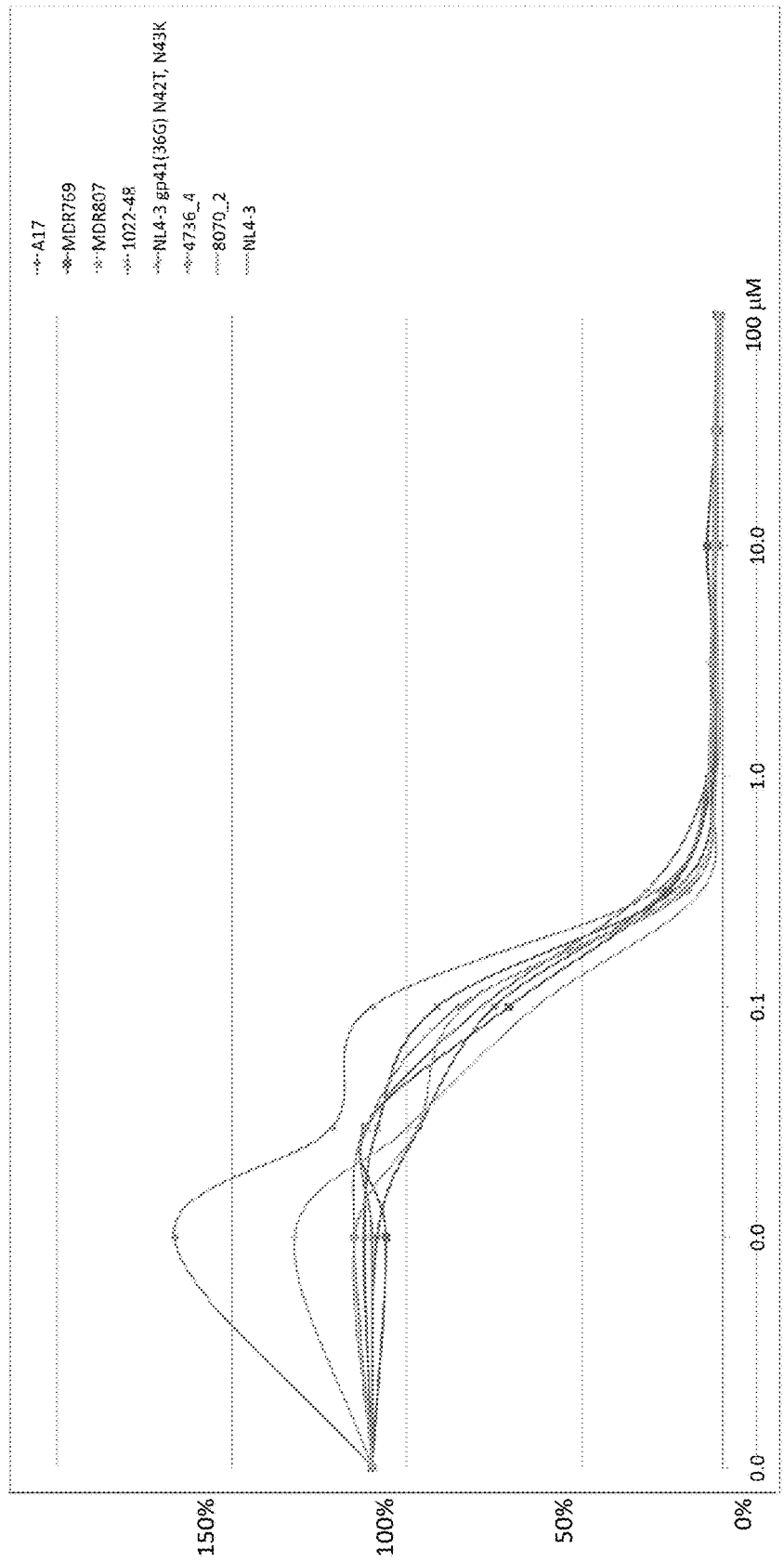
Figures 1, 16B:
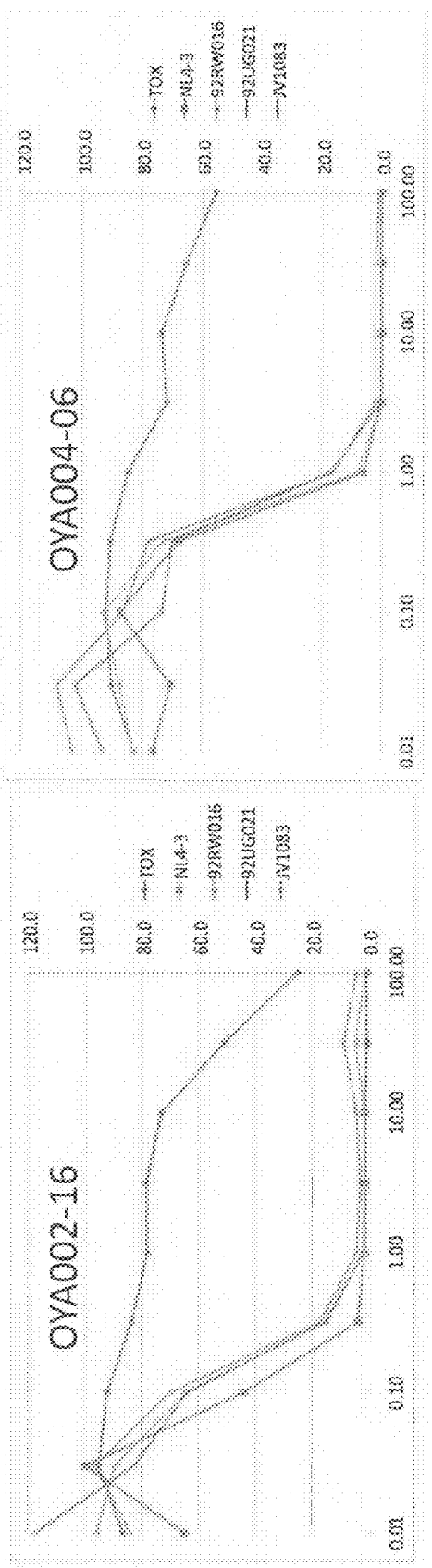
Figures 2, 16B:
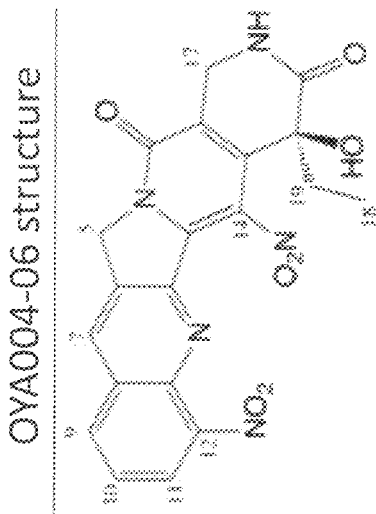

FIG. 14 is an illustration relating to a Next Gen Sequencing for A3G signature mutation profiles. Next Gen Sequencing with the Ion Torrent platform was used to sequence over 27 million bases for each sample. An 885 bp region of Pol was nested PCR amplified from genomic DNA isolated from TZM-bl cells infected in the previous Figures with −Vif virus+A3G (Positive Control) and +Vif virus+A3G & OYA002-16 (OYA002-16) and −Vif−A3G & OYA002-16 (Negative Control). There were 60 possible A3G "GG" signature mutation sites (A3G mediated single-stranded DNA mutations occur preferentially at the 3' C of CC dinucleotide pairs) in the region sequenced. 34 sites were mutated at a rate of 15- to 339-fold over the background mutation rate for the Positive Control. 34 sites were mutated at a rate of 48 to 200-fold over background for the OYA002-16 sample. 21 sites overlapped between the two.

As shown in FIG. 15, efficacy studies of lead scaffold OYA002-16 were conducted. OYA002-16 was evaluated in the low MOI acute infection assay in CEM-SS (low A3G CEM derived T-cells) and A3.01 cells (high A3G CEM derived T-cells, 7-fold more than CEM-SS by qRT-PCR) to determine the relative antiviral activity with compound added every other day for 14 days. Each of the test materials was added to the uninfected cells at three concentrations immediately prior to infection with HIV-1IIIB. Virus replication was monitored by reverse transcriptase (RT) activity on a daily basis over the course of 14 days. DMSO solvent alone was evaluated in parallel. The cytotoxicity of the test materials to uninfected cells treated with the same compound concentrations was evaluated on days 5 and 14 using XTT tetrazolium salt.

As shown in FIGS. 16A-1, 16A-2, 16A-3, 16A-4, 16B-1, and 16B-2, efficacy studies were conducted on OYA002-16 and OYA004-06. These compounds were tested in a standard PBMC cell-based microtiter anti-HIV assay against HIV-1 isolates representing different viral subtypes, and co-receptor tropisms. Test drug dilutions were prepared at a 2× concentration in microtiter tubes and 100 μL of each concentration was placed in appropriate wells using the standard format. 50 μL of a predetermined dilution of virus stock was placed in each test well (final MOI≈0.1). Separate plates were prepared identically without virus for drug cytotoxicity studies using an MTS assay system (Tox). The PBMC cultures were maintained for seven days following infection at 37° C., 5% CO2. After this period, cell-free supernatant samples were collected for analysis of reverse transcriptase activity, and compound cytotoxicity was measured by addition of MTS to the separate cytotoxicity plates for determination of cell viability. The PBMC data analysis includes the calculation of IC50 (50% inhibition of virus replication), IC90 (90% inhibition of virus replication), TC50 (50% cytotoxicity), and therapeutic index values (TI=TC/IC; also referred to as Antiviral Index or AI).

As shown in FIG. 17, toxicity studies were conducted with regard to lead scaffold OYA002-16. All cells are plated on 384-well collagen-coated, tissue culture-treated black walled clear bottomed polystyrene plates. Rat hepatocytes are seeded and dosed on the day they are harvested. Dosing takes place after attachment to the plate. They are treated with test compound at a 10 point dose range of concentrations and incubated for 24 and 48 hrs. HepG2 cells are seeded on the day prior to dosing and are treated with test compound at a 10 point dose range of concentrations and incubated for 24 and 72 hours. At the end of the incubation period, the cells are loaded with the relevant dye/antibody for each cell health marker. The plates are then scanned using an automated High Content Imager, Array Scan® VTI (Thermo Fisher Cellomics). The GSH, ROS, and 5 day toxicity assays were run at 1 time point, 18 hours post-dosing for GSH, 4 hr post-dose for ROS, and 5 days post-drug treatment for the 5 day assay. The largest effect of OYA002-16 is on Cytostasis in HepG2 cells but at antiviral doses in A3.01, there are minimal cell cycle effects (FIG. 15). Moreover, there seems to be minimal effect in Stress and Apoptosis assays along with Viability tests in all tested cell types.

As shown in FIG. 18, stability and solubility studies were conducted on lead scaffold OYA002-16. Plasma Protein Binding (PPB): Test agent is added to plasma. This mixture is dialyzed in a RED Device (Pierce) per the manufacturers' instructions against PBS and incubated on an orbital shaker. After incubation, aliquots from both the plasma and PBS sides are collected, an equal amount of PBS is added to the plasma sample, and an equal volume of plasma is added to the PBS sample. A methanol-containing internal standard (three volumes) is added to precipitate the proteins and release the test agents. After centrifugation, the supernatant is transferred to a new plate and analyzed by LC/MS/MS.

Solubility: 0.7 mg of OYA002-16 was suspended in 100.8 μl Lac-Buffer pH 4.5 or pH 7.4, vortexed for 10 min and warmed-up at 37° C. for 10 min, sonicated for 5 min and vortexed again for 10 min and centrifuged for 10 min. Supernatant was directly injected for concentration measurement. pH 7.4 Solubility: 65-72 μM by UV, 58-63 μM by CLND. pH 4.5 Solubility: 74-92 μM by UV, 74 μM by CLND.

OYA002-16 was found to be 100% stable after 48 h in PBS and after 3 freeze/thaw cycles.

Standard Protocol for Stability Test in PBS Buffer:

For each compound, a 0.250 uM stock solution in DMSO was prepared and sonicated until clear. Then, for each stability test, the cpd was formulated by adding 10 uL of the stock solution to 990 uL of PBS buffer, pH 7.0 and then a 200 uL aliquot was incubated 37° C. for 24 or 48 hrs.

Standard Protocol for Stability Test after 3 Freeze/Thaw Cycles:

For each compound, an aliquot of the stock solution (250 uM in DMSO) was frozen for 24 hrs at −80° C. and thawed for 1 hr, 3 times, then diluted 10 times in 40% CAN and analyzed by HPLC.

Standard Analytical Protocol:

HPLC conditions used for the experiments were as follows: Column: Luna C-18, 150×4.6 from Phenomenex. Eluent: 42% aqueous CAN with 0.75 mM $NH_4OAc$, pH=6.8. Detection: UV at 254 nm. Temperature: 35° C. Flow: 1.5 mL/min. Injection: 20 uL (solubility, freeze/thaw) or 200 uL (stability).

Figure 19:
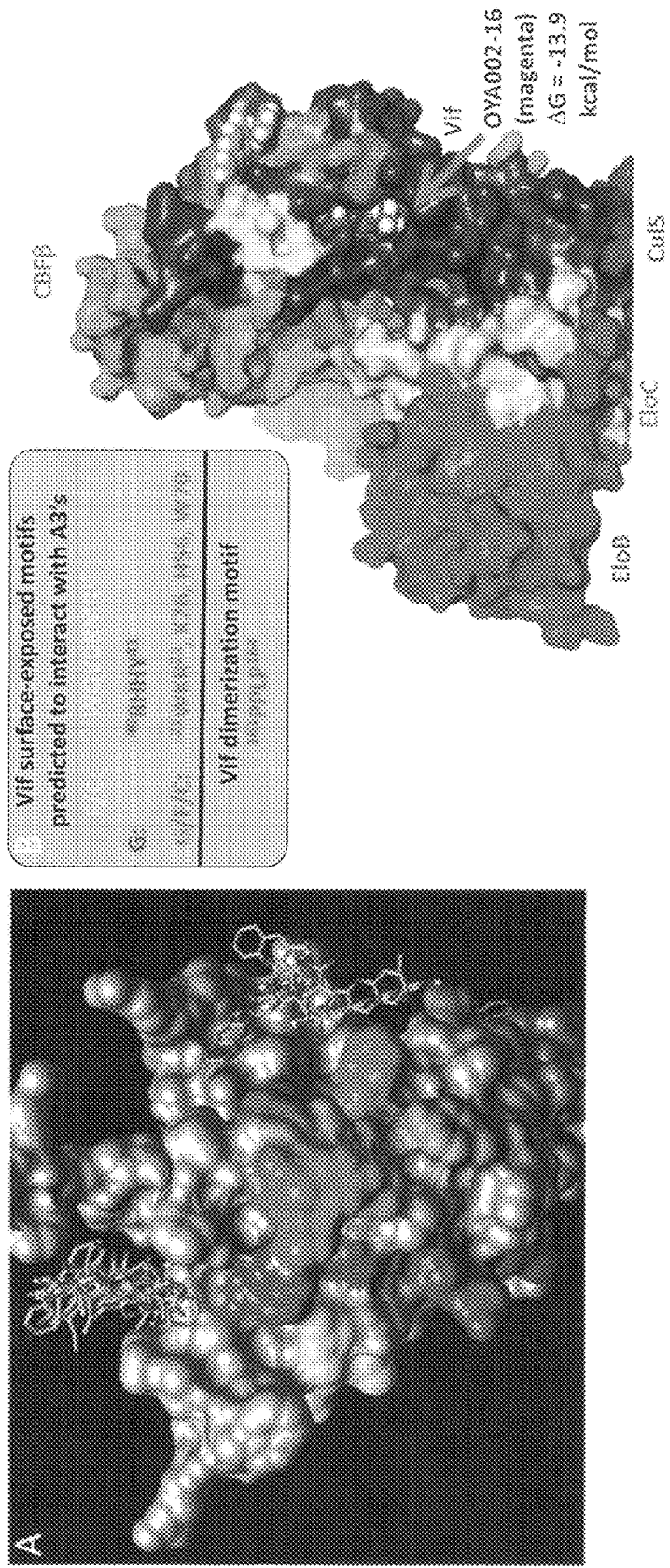
FIGS. 19A and 19B are illustrations showing that unbiased computer docking predicts OYA002-16 scaffold favorably binds to solvent exposed surface of Vif.

As shown in FIGS. 19A and 19B, unbiased computer docking predicted that the OYA002-16 scaffold favorably binds to the solvent exposed surface of Vif. As shown in FIG. 19A, a single pentameric complex of Vif, Elo B, Elo C, CBFb & Cul5 was extracted from the original crystal structure (Guo, et. al, Nature 2014) and saved as a pdb file. Autodock Vina was used to read this file, added polar hydrogen atoms to the pentamer, and created a rectangular grid covering all of the exposed surface to interrogate exclusively this area of the pentameric complex. The 2D structure of OYA002-16 was drawn and used open babel to add missing hydrogens, calculate atomic charges, introduce or subtract hydrogens based on the expected protonated state at physiological pH 7.4, and minimize the molecular structure to obtain their 3D coordinates for in silico docking. Autodock Vina was used to read the surface grid file of Vif along with the files containing the coordinates of OYA002-16. The software automatically docked the compound at every point of the surface grid and was instructed to dock a compound 300 times at every detected binding site with favorable ΔG binding energy outputting a file with the 3D coordinates of the compound according to the interactions at the most favorable binding sites. As shown in FIG. 19B, this unbiased surface probing identified the above binding site where OYA002-16 selectively interacted with a −ΔG value of −13.9 kcal/mol for the lowest energy binding site. Close examination of the crystal structure confirmed that the compounds docks near Vif dimerization residues 161-PPLP-164.

Figures 1, 20A:
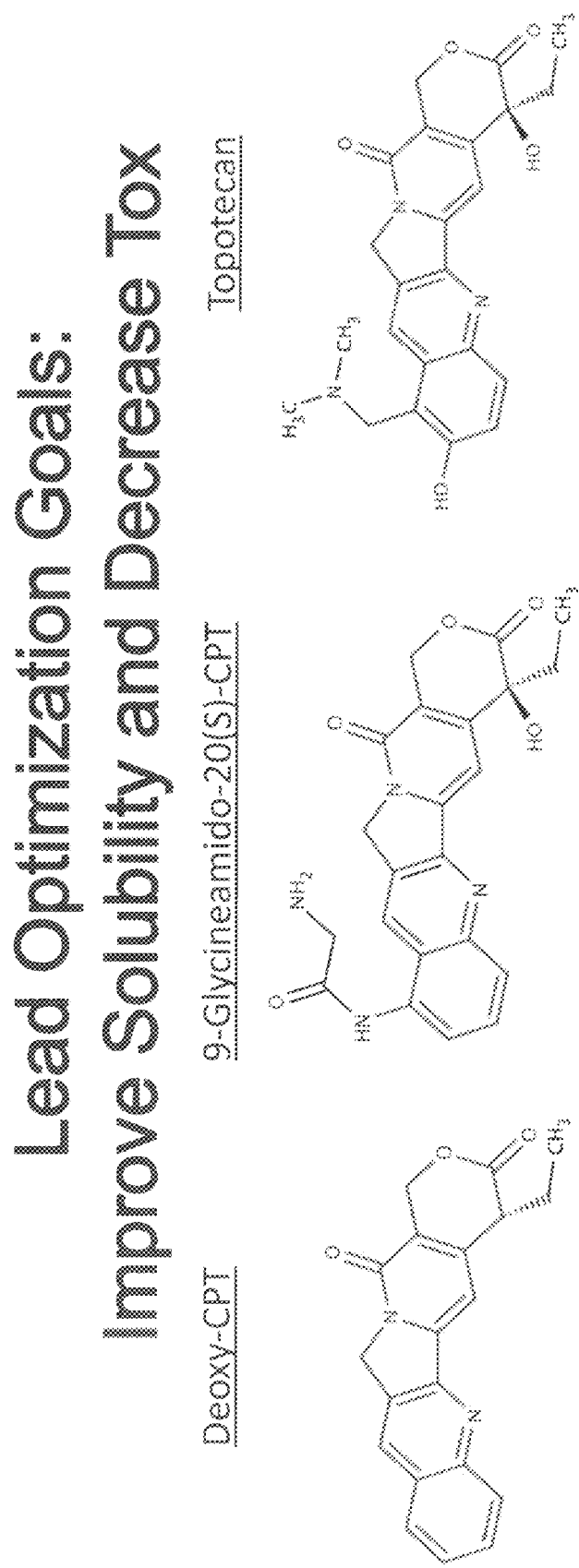
Figures 2, 20A:
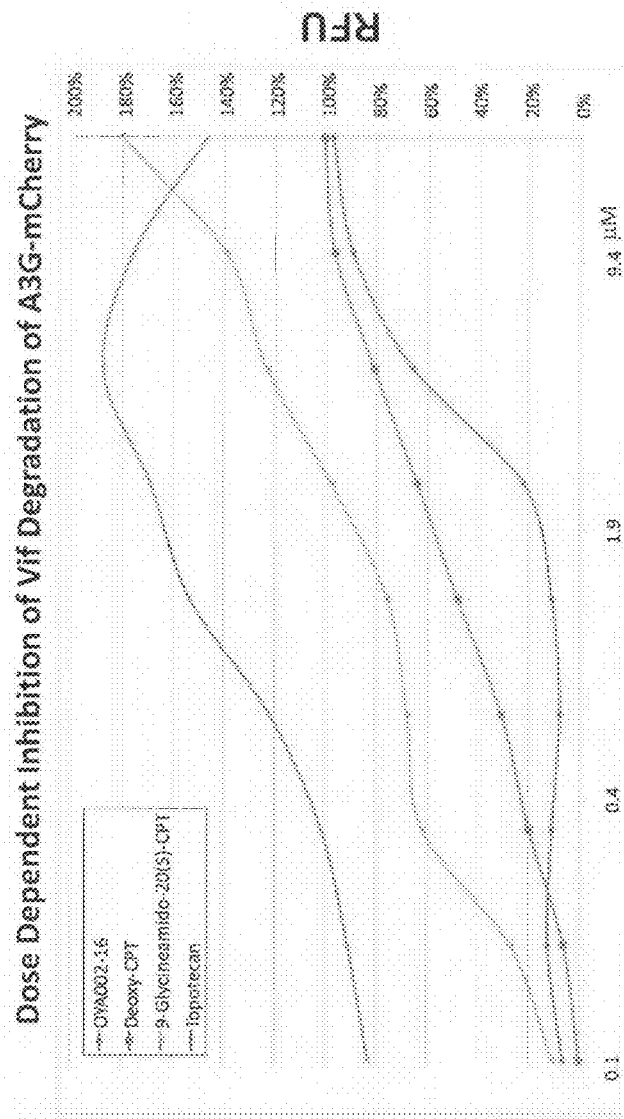

As shown in FIGS. 20A-1, 20A-2, and 20B, lead optimization goals for improving solubility and decreasing toxicity with respect to a Vif inhibitor of the present disclosure were followed. As shown in FIG. 20B, deoxy-CPT was active in 4 of 68 Anti-Cancer Screens at NCI under PubChem BioAssays. Similar to the lactam in OYA002-16, the deoxy at the 20 position eliminates a crucial hydrogen bond with the Topo1 active site. 9-glycineamido-20(S)-CPT was found to be active in 37 of 76 Anti-Cancer Screens at NCI under PubChem BioAssays. The peptide bond off of the 9 position enables solubilizing capabilities with peptide R-groups. Topotecan was found to be active in most Anti-Cancer Screens at NCI under PubChem BioAssays as this is currently an approved chemotherapy drug. The advantage of Topotecan is that is has been optimized for treatment in people with favorable ADME profiles. With the exception of Deoxy-CPT, these CPT derivatives are likely to be too toxic to pursue for an AIDS therapeutic, however, they can be modified with lead attributes for the Vif target (i.e. Lactam-CPT aka OYA002-16). The ultimate goal will be to synthesize and evaluate 5 new compounds for improved toxicity and solubility and favorable DMPK & ADMET.

Figure 21A:
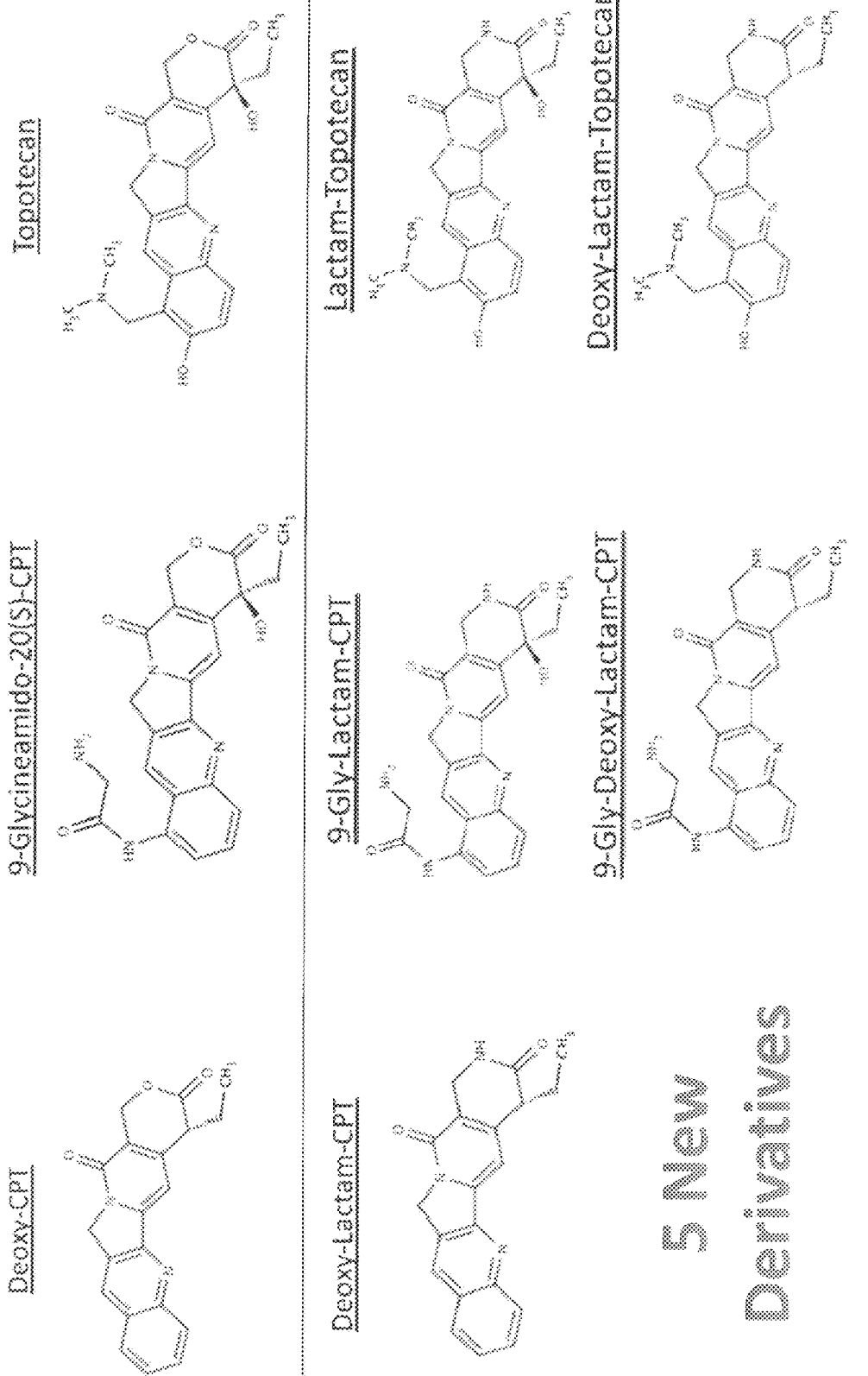
FIG. 21A illustrates derivatives of one small molecule lead scaffold of the present disclosure.
Figure 21B:
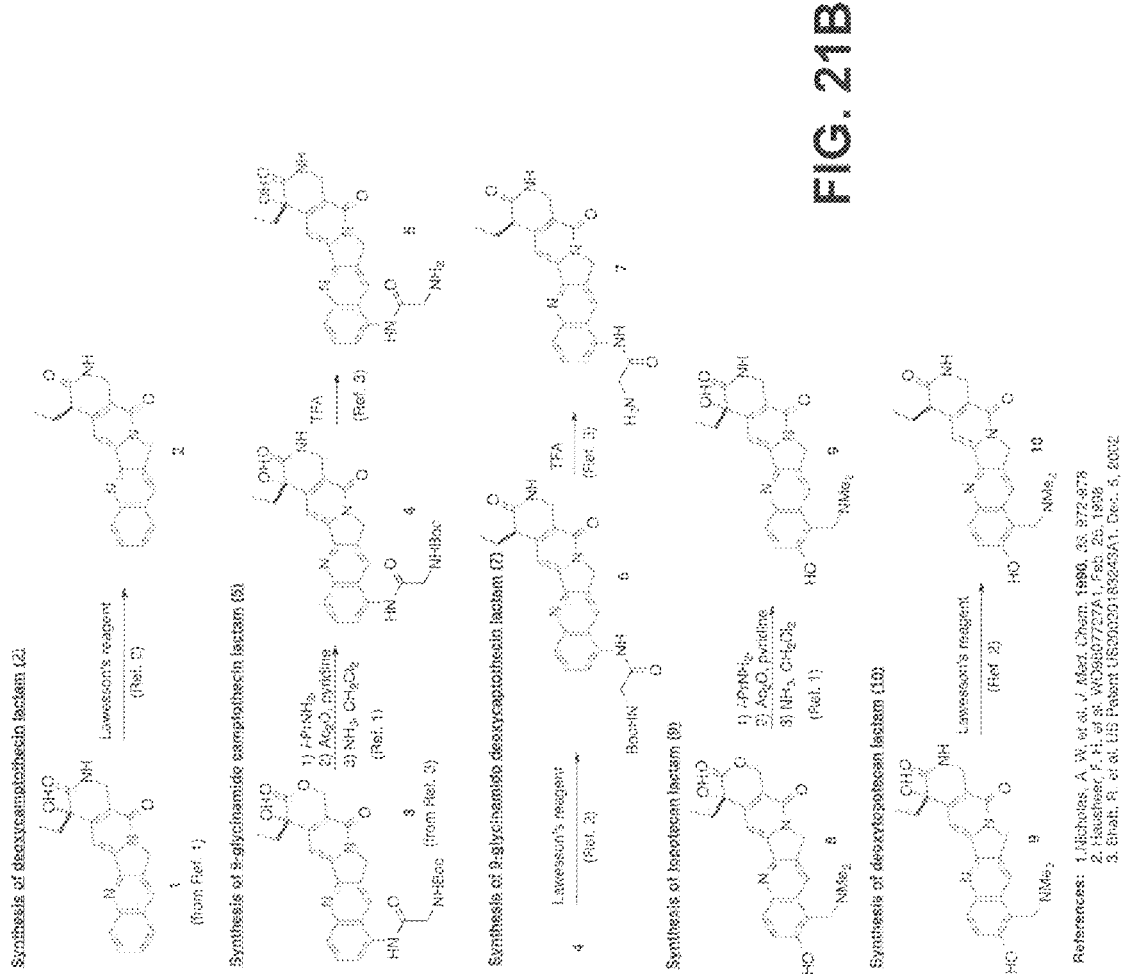
FIG. 21B are schematics of the synthetic pathways of various embodiments of the Vif inhibitor for use in the present invention, including deoxycamptothecin lactam (denoted as formula 2 in the figure) (corresponds to Formula (I-c)), 9-glycinamido camptothecin lactam (denoted as formula 5 in the figure) (corresponds to Formula (I-d)), 9-glycinamido deoxycamptothecin lactam (denoted as formula 7 in the figure) (corresponds to Formula (I-e)), topotecan lactam (denoted as formula 9 in the figure) (corresponds to Formula (I-f)), and deoxytopotecan lactam (denoted as formula 10 in the figure) (corresponds to Formula (I-g)).

FIG. 21A illustrates derivatives of CPT and topotecan that may be useful as Vif inhibitors in accordance with the present invention. As shown in FIG. 21B, various synthetic pathways of various embodiments of the Vif inhibitors for use in the present invention are set forth, including those for deoxycamptothecin lactam (denoted as formula 2 in the figure) (corresponds to Formula (I-c)), 9-glycinamido camptothecin lactam (denoted as formula 5 in the figure) (corresponds to Formula (I-d)), 9-glycinamido deoxycamptothecin lactam (denoted as formula 7 in the figure) (corresponds to Formula (I-e)), topotecan lactam (denoted as formula 9 in the figure) (corresponds to Formula (I-f)), and deoxytopotecan lactam (denoted as formula 10 in the figure) (corresponds to Formula (I-g)).

REFERENCES

Citation of a reference herein shall not be construed as an admission that such reference is prior art to the present invention. All references cited herein are hereby incorporated by reference in their entirety. Below is a listing of references cited herein:

1. Frankel, A. D. and Young, 1 A. (1998) HIV-1: fifteen proteins and an RNA. *Annu Rev Biochem*, 67, 125.
2. Sheehy, A. M., Gaddis, N.C., Choi, 1 D., Malim, M. H. (2002) Isolation of a human gene that inhibits HIV-1 infection and is suppressed by the viral Vifprotein. *Nature*, 418, 646-650.
3. Madani, N. and Kabat, D. (1998) An endogenous inhibitor of human immunodeficiency virus in human lymphocytes is overcome by the viral Vif protein. *J Virol*, 72, 10251-10255.
4. Simon, 1 H., Gaddis, N. C., Fouchier, R. A. and Malim, M. H. (1998) Evidence for a newly discovered cellular anti-HIV-1 phenotype. *Nat Med*, 4, 1397-1400.
5. Soya, P. and Volsky, D. 1 (1993) Efficiency of viral DNA synthesis during infection of permissive and nonpermissive cells with vif-negative human immunodeficiency virus type 1. *J Virol*, 67, 6322-6326.
6. von Schwedler, D., Song, 1, Aiken, C. and Trono, D. (1993) Vif is crucial for human immunodeficiency virus type 1 proviral DNA synthesis in infected cells. *J Virol*, 67, 4945-4955.
7. Simon, 1 H. and Malim, M. H. (1996) The human immunodeficiency virus type 1 Vif protein modulates the postpenetration stability of viral nucleoprotein complexes. *J Virol*, 70, 5297-5305.
8. Courcoul, M., Patience, c., Rey, F., Blanc, D., Harmache, A., Sire, J., Vigne, R. and Spire, B. (1995) Peripheral blood mononuclear cells produce normal amounts of defective Vif-human immunodeficiency virus type 1 particles which are restricted for the preretrotranscription steps. *J Virol*, 69, 2068-2074.
9. Mangeat, B., Turelli, P., Caron, G., Friedli, M., Perrin, L. and Trono, D. (2003) Broad antiretroviral defence by human APOBEC3G through lethal editing of nascent reverse transcripts. *Nature*, 424, 99103.
10. Harris, R. S., Bishop, K. N., Sheehy, A. M., Craig, H. M., Petersen-Mahrt, S. K., Watt, L N., Neuberger, M. S. and Malim, M. H. (2003) DNA deamination mediates innate immunity to retroviral infection. *Cell*, 113, 803-809.
11. Zhang, H., Yang, B., Pomerantz, R. 1, Zhang, c., Arunachalam, S. C. and Gao, L. (2003) The cytidine deaminase CEM15 induces hypermutation in newly synthesized HIV-1 DNA. *Nature*, 424, 94-98.
12. Jarmuz, A., Chester, A., Bayliss, 1, Gisboume, 1, Dunham, I., Scott, J. and Navaratnam, N. (2002) An anthropoid-specific locus of orphan C to D RNA-editing enzymes on chromosome 22. *Genomics*, 79, 285-296.
13. Wedekind, J. E., Dance, G. S., Sowden, M. P. and Smith, H. C. (2003) Messenger RNA editing in mammals: new members of the APOBEC family seeking roles in the family business. *Trends Genet*, 19, 207-216.
14. Pham, P., Chelico, L. and Goodman, M. F. (2007) DNA deaminases AID and APOBEC3G act processively on single-stranded DNA. *DNA Repair (Amst)*, 6, 689-692; author reply 693-684.
15. Chelico, L., Pham, P., Calabrese, P. and Goodman, M. P. (2006) APOBEC3G DNA deaminase acts processively 3'→5' on single-stranded DNA. *Nat Struct Mol Biol*, 13, 392-399.
16. Suspene, R., Rusniok, c., Vartanian, J. P. and Wain-Hobson, S. (2006) Twin gradients in APOBEC3 edited HIV-1 DNA reflect the dynamics of lentiviral replication. *Nucleic Acids Res*, 34, 4677-4684.
17. Yu, Q., Konig, R., Pillai, S., Chiles, K., Kearney, M., Palmer, S., Richman, D., Coffin, J. M. and Landau, N. R. (2004) Single-strand specificity of APOBEC3G accounts for minus-strand deamination of the HIV genome. *Nat Struct Mol Biol*, 11, 435-442.
18. Willetts, K. E., Rey, F., Agostini, I., Navarro, J. M., Baudat, Y., Vigne, R. and Sire, 1 (1999) DNA repair enzyme uracil DNA glycosylase is specifically incorporated into human immunodeficiency virus type 1 viral particles through a Vpr-independent mechanism. *J Virol*, 73, 1682-1688.
19. Bouhamdan, M., Benichou, S., Rey, F., Navarro, J. M., Agostini, I., Spire, B., Camonis, 1, Slupphaug, G., Vigne, R., Benarous, R. et al. (1996) Human immunodeficiency virus type 1 Vpr protein binds to the uracil DNA glycosylase DNA repair enzyme. *J Virol*, 70, 697-704.
20. Bishop, K. N., Holmes, R. K. and Malim, M. H. (2006) Antiviral potency of APOBEC proteins does not correlate with cytidine deamination. *J Virol*, 80, 8450-8458.
21. Guo, F., Cen, S., Niu, M., Saadatmand, 1 and Kleiman, L. (2006) Inhibition of formula-primed reverse transcription by human APOBEC3G during human immunodeficiency virus type 1 replication. *J Virol*, 80, 11710-11722.
22. Li, X. Y., Guo, F., Zhang, L., Kleiman, L. and Cen, S. (2007) APOBEC3G inhibits DNA strand transfer during HIV-1 reverse transcription. *J Biol Chem*, 44, 32065-32074.
23. Mariani, R., Chen, D., Schrofelbauer, B., Navarro, F., Konig, R., Bollman, B., Munk, C., NymarkMcMahon, H. and Landau, N. R. (2003) Species-specific exclusion of APOBEC3G from HIV-1 virions by Vif. *Cell*, 114, 21-31.

24. Stopak, K., De Noronha, c., Yonemoto, W., and Greene, W. c. (2003) HIV-1 Vif Blocks the Antiviral Activity of APOBEC3G by Impairing both Its Translation and Intracellular Stability. *Mol Cell,* 12, 591601.

25. Yu, X., Yu, Y., Liu, B., Luo, K., Kong, W., Mao, P. and Yu, X. F. (2003) Induction of APOBEC3G ubiquitination and degradation by an HIV-1 Vif-Cul5-SCF complex. *Science,* 302, 1056-1060.

26. Mehle, A., Goncalves, 1, Santa-Marta, M., McPike, M. and Gabuzda, D. (2004) Phosphorylation of a novel SOCS-box regulates assembly of the HIV-1 Vif-Cul5 complex that promotes APOBEC3G degradation. *Genes Dev,* 18, 2861-2866.

27. Mehle, A., Thomas, E. R., Rajendran, K. S. and Gabuzda, D. (2006) A zinc-binding region in Vifbinds Cul5 and determines cullin selection. *J Biol Chem,* 281, 17259-17265.

28. Dang, Y., Siew, L. M. and Zheng, Y. H. (2008) APOBEC3G is degraded by the proteasomal pathway in a Vif-dependent manner without being polyubiquitylated. *J Biol Chem,* 283, 13124-13131.

29. Schrofelbauer, B., Chen, D. and Landau, N. R. (2004) A single amino acid of APOBEC3G controls its species-specific interaction with virion infectivity factor (Vif). *Proc Natl Acad Sci USA,* 101, 39273932.

30. Xu, H., Svarovskaia, E. S., Barr, R., Zhang, Y., Khan, M. A., Strebel, K. and Pathak, V. K. (2004) A single amino acid substitution in human APOBEC3G antiretroviral enzyme confers resistance to HIV-1 virion infectivity factor-induced depletion. *Proc Natl Acad Sci USA,* 101, 5652-5657.

31. Mangeat, B., Turelli, P., Liao, S. and Trono, D. (2004) A single amino acid determinant governs the species-specific sensitivity of APOBEC3G to Vif action. *J Biol Chem,* 279, 14481-14483.

32. Huthoff, H. and Malim, M. H. (2007) Identification of amino acid residues in APOBEC3G required for regulation by human immunodeficiency virus type 1 Vif and Virion encapsidation. *J Virol,* 81, 38073815.

33. Russell, R. A. and Pathak, V. K. (2007) Identification of two distinct human immunodeficiency virus type 1 Vif determinants critical for interactions with human APOBEC3G and APOBEC3F. *J Virol,* 81, 82018210.

34. Schrofelbauer, B., Senger, T., Manning, G. and Landau, N. R. (2006) Mutational alteration of human immunodeficiency virus type 1 Vif allows for functional interaction with nonhuman primate APOBEC3G. *J Virol,* 80, 5984-5991.

35. Pery, E., Rajendran, K. S., Brazier, A. 1 and Gabuzda, D. (2009) Regulation of APOBEC3 proteins by a novel YXXL motif in human immunodeficiency virus type 1 Vif and simian immunodeficiency virus SIVagm Vif. *J Virol,* 83, 2374-2381.

36. He, Z., Zhang, W., Chen, G., Xu, R. and Yu, X. F. (2008) Characterization of conserved motifs in HIV-1 Vif required for APOBEC3G and APOBEC3F interaction. *J Mol Biol,* 381, 1000-10 11.

37. Yang, S., Sun, Y. and Zhang, H. (2001) The multimerization of human immunodeficiency virus type I Vif protein: a requirement for Vif function in the viral life cycle. *J Biol Chem,* 276, 4889-4893.

38. Yang, B., Gao, L., Li, L., Lu, Z., Fan, X., Patel, C. A., Pomerantz, R J., DuBois, G. C. and Zhang, H. (2003) Potent suppression of viral infectivity by the peptides that inhibit multimerization of human immunodeficiency virus type 1 (HIV-1) Vifproteins. *J Biol Chem,* 278, 6596-6602.

39. Miller, l H., Presnyak, V. and Smith, H. C. (2007) The dimerization domain of HI V-I viral infectivity factor Vif is required to block virion incorporation of APOBEC3G. *Retrovirology,* 4, 81.

40. Donahue, 1 P., Vetter, M. L., Mukhtar, N. A. and D'Aquila, R. T. (2008) The HIV-1 VifPPLP motif is necessary for human APOBEC3G binding and degradation. *Virology,* 377, 49-53.

41. Mehle, A, Wilson, H., Zhang, c., Brazier, A 1, McPike, M., Pery, E. and Gabuzda, D. (2007) Identification of an APOBEC3G binding site in human immunodeficiency virus type 1 Vif and inhibitors of Vif-APOBEC3G binding. *J Virol,* 81, 13235-13241.

42. Nathans, R, Cao, H., Sharova, N., Ali, A, Sharkey, M., Stranska, R., Stevenson, M. and Rana, T. M. (2008) Small-molecule inhibition of HIV-1 Vif. *Nat Biotechnol,* 26, 1187-1192.

43. Luo, K., Liu, B., Xiao, Z., Yu, Y., Yu, X., Gorelick, R. and Yu, X. P. (2004) Amino-terminal region of the human immunodeficiency virus type 1 nucleocapsid is required for human APOBEC3G packaging. *J Virol,* 78, 11841-11852.

44. Cen, S., Guo, F., Niu, M., Saadatmand, 1, Deflassieux, 1 and Kleiman, L. (2004) The interaction between HIV-1 Gag and APOBEC3G. *J Biol Chem,* 279, 33177-33184.

45. Bennett, R P., Presnyak, V., Wedekind, 1 E. and Smith, H. C. (2008) Nuclear Exclusion of the HIV-1 host defense factor APOBEC3G requires a novel cytoplasmic retention signal and is not dependent on RNA binding. *J Biol Chem,* 283, 7320-7327.

46. Bennett, R P., Diner, E., Sowden, M. P., Lees, J. A, Wedekind, 1 E. and Smith, H. C. (2006) APOBEC-1 and AID are nucleo-cytoplasmic trafficking proteins but APOBEC3G cannot traffic. *Biochem Biophys Res Commun,* 350, 214-219.

47. Oppezzo, P., Vuillier, F., Vasconcelos, Y., Dumas, G., Magnac, C., Payelle-Brogard, B., Pritsch, O. and Dighiero, G. (2003) Chronic lymphocytic leukemia B cells expressing AID display dissociation between class switch recombination and somatic hypermutation. *Blood,* 101, 4029-4032.

48. Okazaki, L M., Hiai, H., Kakazu, N., Yamada, S., Muramatsu, M., Kinoshita, K. and Honjo, T. (2003) Constitutive expression of AID leads to tumorigenesis. *J Exp Med,* 197, 1173-1181.

49. Yamanaka, S., M. Balestra, L. Ferrell, J. Fan, K. S. Arnold, S. Taylor, 1 M. Taylor, Innerarity, T. L. (1995) Apolipoprotein B mRNA editing protein induces hepatocellular carcinoma and dysplasia in transgenic animals. *Proc. Natl. Acad. Sci USA,* 92, 8483-8487.

50. Yamanaka, S., Poksay, K S., Arnold, K S. and Innerarity, T. L. (1997) A novel translational repressor mRNA is edited extensively in livers containing tumors caused by the transgene expression of the apoB mRNA-editing enzyme. *Genes Dev,* 11, 321-333.

51. Babbage, G., Ottensmeier, C. H., Blaydes, 1, Stevenson, F. K. and Sahota, S. S. (2006) Immunoglobulin heavy chain locus events and expression of activation-induced cytidine deaminase in epithelial breast cancer cell lines. *Cancer Res,* 66, 3996-4000.

52. Duquette, M. L., Pham, P., Goodman, M. P. and Maizels, N. (2005) AID binds to transcription-induced structures in c-MYC that map to regions associated with translocation and hypermutation. *Oncogene,* 24, 5791-5798.

53. Rucci, P., Cattaneo, L., Marrella, V., Sacco, M. G., Sobacchi, C., Lucchini, F., Nicola, S., Della Bella, S., Villa, M. L., Imberti, L. et al. (2006) Tissue-specific sensitivity to AID expression in transgenic mouse models. *Gene*, 377, 150-158.

54. Ganesan, S., Ameer-Beg, S. M., Ng, T. T., Vojnovic, B. and Wouters, F. S. (2006) A dark yellow fluorescent protein (YFP)-based Resonance Energy-Accepting Chromoprotein (REACh) for Forster resonance energy transfer with GFP. *Proc Natl Acad Sci USA*, 103, 4089-4094.

55. Lee, P. A, Tullman-Ercek, D. and Georgiou, G. (2006) The bacterial twin-arginine translocation pathway. *Annu Rev Microbiol*, 60, 373-395.

56. DeLisa, M. P., Tullman, D. and Georgiou, G. (2003) Folding quality control in the export of proteins by the bacterial twin-arginine translocation pathway. *Proc Natl Acad Sci USA*, 100, 6115-6120.

57. Waraho, D. and Delisa, M. P. (2009) Versatile selection technology for intracellular protein-protein interactions mediated by a unique bacterial hitchhiker transport mechanism. *Proc Natl Acad Sci USA*, 106, 3692-3697.

58. Lee, L. L., Ha, H., Chang, Y. T. and DeLisa, M. P. (2009) Discovery of amyloid-beta aggregation inhibitors using an engineered assay for intracellular protein folding and solubility. *Protein Sci*, 18, 277286.

59. Bennett, R P., Salter, 1 D., Liu, X., Wedekind, 1 E. and Smith, H. C. (2008) APOBEC3G subunits selfassociate via the C-terminal deaminase domain. *J Biol Chem*, 283, 33329-33336.

60. Soros, V. B., Yonemoto, W. and Greene, W. C. (2007) Newly synthesized APOBEC3G is incorporated into HIV virions, inhibited by HIV RNA, and subsequently activated by RNase H. *PLoS Pathog*, 3, e15.

61. Wichroski, M J., Ichiyama, K. and Rana, T. M. (2005) Analysis of HIV-1 viral infectivity factormediated proteasome-dependent depletion of APOBEC3G: correlating function and subcellular localization. *J Biol Chem*, 280, 8387-8396.

62. Platt, E. J., Wehrly, K., Kuhmann, S. E., Chesebro, B. and Kabat, D. (1998) Effects of CCR5 and CD4 cell surface concentrations on infections by macrophage tropic isolates of human immunodeficiency virus type 1. *J Virol*, 72, 2855-2864.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating HIV infection in a patient by inhibiting Vif self-association in a cell, said method comprising:
   administering to a patient in need of such treatment a therapeutically effective amount of a compound of Formula (I-a):

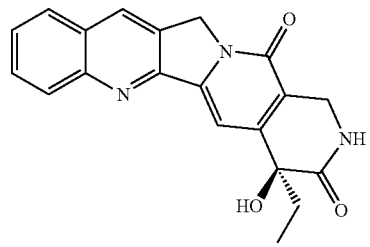

(I-a)

or a pharmaceutically acceptable salt thereof.

2. A method for inhibiting infectivity of a lentivirus in a cell, said method comprising:
   contacting a cell with an antiviral-effective amount of a compound of Formula (I-a):

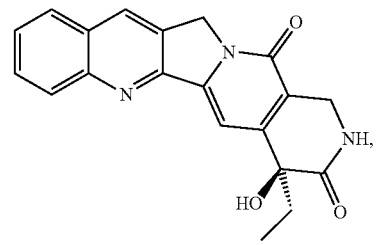

(I-a)

or a pharmaceutically acceptable salt thereof.

* * * * *